(12) United States Patent
Matthews et al.

(10) Patent No.: US 12,226,448 B2
(45) Date of Patent: *Feb. 18, 2025

(54) PEANUT ORAL IMMUNOTHERAPY DOSING SCHEDULE FOR MISSED DOSES

(71) Applicant: SOCIÉTÉ DES PRODUITS NESTLÉ S.A., Vevey (CH)

(72) Inventors: John Graham Matthews, San Francisco, CA (US); Kari Rose Brown, Cary, NC (US); Anoshie Ratnayake, Newport Beach, CA (US); Daniel Adelman, Redwood City, CA (US)

(73) Assignee: Société des Produits Nestlé S.A., Vevey (CH)

( * ) Notice: Subject to any disclaimer, the term of this patent is extended or adjusted under 35 U.S.C. 154(b) by 889 days.

This patent is subject to a terminal disclaimer.

(21) Appl. No.: 16/721,805

(22) Filed: Dec. 19, 2019

(65) Prior Publication Data

US 2020/0230206 A1 Jul. 23, 2020

Related U.S. Application Data

(60) Provisional application No. 62/783,102, filed on Dec. 20, 2018.

(51) Int. Cl.
*A61K 38/16* (2006.01)
*A61K 9/00* (2006.01)

(52) U.S. Cl.
CPC .......... *A61K 38/168* (2013.01); *A61K 9/0053* (2013.01)

(58) Field of Classification Search
CPC .................................................. A61K 38/168
See application file for complete search history.

(56) References Cited

U.S. PATENT DOCUMENTS

| | | | |
|---|---|---|---|
| 3,809,767 A | 5/1974 | Sair et al. | |
| 9,198,869 B2 | 12/2015 | Walser | |
| 9,481,716 B2 | 11/2016 | Clark | |
| 9,492,535 B2* | 11/2016 | Walser | G01N 33/6893 |
| 9,815,894 B2 | 11/2017 | O'brien et al. | |
| 9,949,958 B2 | 4/2018 | Forbes | |
| 9,955,718 B2 | 5/2018 | Gillespie | |
| 9,999,600 B2 | 6/2018 | Sosin | |
| 10,086,068 B2 | 10/2018 | Walser | |
| 10,266,588 B2 | 4/2019 | Macdonald et al. | |
| 10,278,964 B2 | 5/2019 | Mann et al. | |
| 10,286,018 B2 | 5/2019 | Smith | |
| 10,449,118 B2 | 10/2019 | Walser | |
| D866,320 S | 11/2019 | Bennet et al. | |
| D866,321 S | 11/2019 | Bennet et al. | |
| D866,322 S | 11/2019 | Bennet et al. | |
| 10,512,686 B2 | 12/2019 | Walser | |
| 10,653,773 B2 | 5/2020 | Walser | |
| 10,918,676 B2 | 2/2021 | Raff | |
| 11,141,352 B2 | 10/2021 | Walser et al. | |
| 11,229,673 B2 | 1/2022 | Birchwood | |
| 11,369,676 B2* | 6/2022 | Dilly | A61K 9/0053 |
| 2002/0018778 A1 | 2/2002 | Caplan | |
| 2004/0166123 A1 | 8/2004 | Jacobi | |
| 2004/0234548 A1 | 11/2004 | Caplan | |
| 2008/0317878 A1 | 12/2008 | Li et al. | |
| 2009/0111702 A1 | 4/2009 | Sampson et al. | |
| 2011/0243994 A1 | 10/2011 | Asari et al. | |
| 2012/0164306 A1 | 6/2012 | Girsh | |
| 2013/0090344 A1 | 4/2013 | Thakur et al. | |
| 2014/0093541 A1 | 4/2014 | Clark | |
| 2014/0207105 A1 | 7/2014 | Laulicht et al. | |
| 2014/0271721 A1 | 9/2014 | Walser | |
| 2014/0271836 A1 | 9/2014 | Walser | |
| 2014/0363470 A1 | 12/2014 | Koppelman et al. | |
| 2015/0343075 A1 | 12/2015 | Raff | |
| 2016/0030289 A1 | 2/2016 | Walser | |
| 2016/0051593 A1 | 2/2016 | Raff | |
| 2016/0051639 A1 | 2/2016 | Raff | |
| 2016/0263212 A1 | 9/2016 | Friedman et al. | |
| 2017/0021012 A1 | 1/2017 | Walser | |
| 2018/0042816 A1 | 2/2018 | Walser | |
| 2018/0118760 A1* | 5/2018 | Kawai | C07F 9/6561 |
| 2018/0200361 A1 | 7/2018 | Simon | |
| 2019/0167785 A1 | 6/2019 | Dilly | |
| 2019/0175723 A1 | 6/2019 | Walser | |
| 2019/0192652 A1 | 6/2019 | Walser | |
| 2019/0247444 A1 | 8/2019 | Raff | |

(Continued)

FOREIGN PATENT DOCUMENTS

JP 2003128697 A 5/2003
JP 2006519187 A 8/2006

(Continued)

OTHER PUBLICATIONS

Montgomery, 2007, Immunotherapy Safety for the Primary Care Provider, pp. 1-292.*
Cox, Allergen immunotherapy: A practice parameter third update, J Allergy Clin Immunol. Jan. 2011, S1-S55.*
Bird et al., J. Allergy Clin. Immunol. Pract., vol. 6, No. 2, p. 476-485 (2018).*
Vickery et al., AR101 Oral Immunotherapy for Peanut Allergy, N. Engl. J. Med. 2018; 379:1991-2001.*
Hoffman, NIH Report Aug. 10, 2016.*
Andorf, Allergy, Asthma, & Clinical Immunology (2017), 13, 52/1-52/10.*

(Continued)

*Primary Examiner* — Nizal S Chandrakumar
(74) *Attorney, Agent, or Firm* — Morgan, Lewis & Bockius LLP

(57) ABSTRACT

The present disclosure relates to improved oral immunotherapy methods for treating peanut allergy. In certain embodiments, the disclosure provides methods for continuing an oral immunotherapy for the treatment of a peanut allergy after missing a scheduled oral administration of one or more consecutive doses of a pharmaceutical composition comprising peanut protein.

20 Claims, 3 Drawing Sheets

(56) References Cited

U.S. PATENT DOCUMENTS

| | | | |
|---|---|---|---|
| 2020/0030187 | A1 | 1/2020 | Bennett |
| 2020/0054738 | A1 | 2/2020 | Adelman |
| 2020/0129378 | A1 | 4/2020 | Walser |
| 2020/0368304 | A1 | 11/2020 | Birchwood |
| 2021/0052722 | A1 | 2/2021 | Walser et al. |
| 2022/0221468 | A1 | 7/2022 | Dilly |

FOREIGN PATENT DOCUMENTS

| | | | |
|---|---|---|---|
| JP | 2009522258 | A | 6/2009 |
| JP | 2011225525 | A | 11/2011 |
| JP | 2013505897 | A | 2/2013 |
| JP | 2013519649 | A | 5/2013 |
| JP | 2014509606 | A | 4/2014 |
| NO | 2010059534 | A3 | 1/2011 |
| NO | 2020131917 | A1 | 6/2020 |
| WO | 199215285 | A1 | 9/1992 |
| WO | 2004075875 | A1 | 9/2004 |
| WO | 2007075171 | A1 | 7/2007 |
| WO | 2010059534 | A2 | 5/2010 |
| WO | 2010069595 | A1 | 6/2010 |
| WO | 2011012990 | A2 | 2/2011 |
| WO | 2011012990 | A3 | 6/2011 |
| WO | 2011098499 | A1 | 8/2011 |
| WO | 2012001074 | A2 | 1/2012 |
| WO | 2012001074 | A3 | 3/2012 |
| WO | 2012123759 | A1 | 9/2012 |
| WO | 2013087119 | A1 | 6/2013 |
| WO | 2013087837 | A1 | 6/2013 |
| WO | WO2014159607 | A1 | 10/2014 |
| WO | WO2014159609 | A1 | 10/2014 |
| WO | WO2015187736 | A1 | 12/2015 |
| WO | WO2016033094 | A1 | 3/2016 |
| WO | WO2018132733 | A1 | 7/2018 |
| WO | 2018146274 | A1 | 8/2018 |
| WO | WO2019089978 | A1 | 5/2019 |
| WO | WO2020023925 | A1 | 1/2020 |
| WO | WO2020037151 | A1 | 2/2020 |

OTHER PUBLICATIONS

Chan, International Reviews of Immunology (2018), 37(6), 279-290.*
Collier, CMAJ Jun. 1, 20131; 185(9): E385-E386.*
Paracelsus, "Die dritte Defension wegen des Schreibens der neuen Rezepte," Septem Defensiones 1538. Werke Bd. 2, Darmstadt 1965.*
Swarbrick, Drugs Pharm. Sci., 2006.*
Collier, CMAJ Jun. 11, 2013; 185(9): E385-E386.*
Feldman, Health Affairs Jun. 2022 41:6, 801-804.*
Dwivedi, Technology in Society 32 (2010) 324-330.*
Bird, A et al. (2018). "Efficacy and Safety of AR101 in Oral Immunotherapy for Peanut Allergy: Results of ARC001, a Randomized, Double-Blind, Placebo-Controlled Phase 2 Clinical Trial," The Journal of Allergy and Clinical Immunology: In Practice. 6(2):476-485.
U.S. Appl. No. 16/453,871, Walser et al., filed Jun. 26, 2019. (Copy not submitted herewith pursuant to waiver of 37 C.F.R. § 1.98(a)(2)(iii) issued by the Office on Sep. 21, 2004).
U.S. Appl. No. 16/842,675, Walser et al., filed Mar. 7, 2020.(Copy not submitted herewith pursuant to waiver of 37 C.F.R. § 1.98(a)(2)(iii) issued by the Office on Sep. 21, 2004).
Vickery, B.P. et al. (Nov. 22, 2018). "AR101 Oral Immunotherapy for Peanut Allergy," The New England Journal of Medicine 379(21):1991-2001.
Adelman, D.C. (Oct. 17, 2018). "Efficacy and Safety of AR101 in Peanut Allergy: Resultsfrom a Phase 3, Randomized, Double-Blind Placebo Controlled Trial (PALISDAE)," InternationalFood Allergy & Anaphylaxis Alliance (IFAAA) Meeting, Copenhagen, Denmark, 23 pages.
Altschul, A.S. et al. (Sep. 2001). "Manufacturing and Labeling Issues for Commercial Products: Relevance to Food Allergy," J. Allergy Clin. Immunol. 108(3):468, 1 page.
Anagnostou, K. et al. (2011). "Efficacy and Safety of High-Dose Peanut Oral Immunotherapy With Factors Predicting Outcome," Clinical & Experimental Allergy, 41:1273-1281.
Anagnostou, K. et al. (Apr. 12, 2014, e-pub. Jan. 30, 2014). "Assessing The Efficacy of Oral Immunotherapy for the Desensitization of Peanut Allergy in Children (Stop II): A Phase 2 Randomized Controlled Trial," The Lancet 383(9925):1297-1304.
AU2014240404, Patent Examination Report No. 1, mailed Mar. 31, 2013, 3 pages.
Avery, N.J. et al. (Oct. 2003). "Assessment of Quality of Life in Children With Peanut Allergy," Ped. Allergy Immunol. 14(5):378-382. Abstract Only, 2 pages.
Ballmer-Weber B.K. et al. (2015). "IgE Recognition Patterns in Peanut Allergy Are Age Dependent: Perspectives of the Europrevall Study," Allergy 70:391-407.
Bernard, H. et al. (2007, e-pub. Oct. 20, 2007). "Identification of a New Natural Ara h6 Isoform and of Its Proteolytic Product as Major Allergens in Peanut," J. of Agricultural and Food Chem. 55(23):9663-9669.
Beyer, K. et al. (Oct. 19, 2018). "Adrenaline Use and Reaction-Severity During the ExitDouble-Blind, Placebo-Controlled Food Challenge (DBPCFC) with Peanut in Subjects Aged 4-17 Years in PALISADE, a Phase 3, Randomised, Double-Blind, Placebo-Controlled Trial, "presented at the Food Allergy and Anaphylaxis Meeting (FAAM), Copenhagen Denmark, 13 pages.
Blumchen, K. et al. (Jul. 2010). "Oral Peanut Immunotherapy in Children With Peanut Anaphylaxis," J Allergy Clin Immunol. 126(1):83-91.
Bock, S.A. et al. (Dec. 1988). "Double-Blind, Placebo-Controlled Food Challenge (DBPCFC) as an Office Procedure: A Manual," J Allergy Clin Immunol. 82(6):986-997.
Bock, S.A. et al. (Jan. 2001). "Fatalities Due to Anaphylactic Reactions to Foods," J Allergy Clin. Immunol. 107 (1):191-193.
Bock, S.A. et al. (Oct. 1990). "Patterns of Food Hypersensitivity During Sixteen Years of Double-Blind, Placebo-Controlled Food Challenges," J Pediatr. 117(4):561-567.
Bollinger, M.E. et al. (Mar. 2006). "The Impact of Food Allergy on the Daily Activities of Children and Their Families," Ann. Allergy Asthma Immunol. 96(3):415-421. Abstract Only, 2 pages.
Bousquet, J. (2004). "Chapter 6—Primary and Secondary Prevention of Allergy and Asthma by Allergen Therapeutic Vaccines," in Allergens and Allergen Immunotherapy 18:105-114.
Boyce, J.A. et al. (Dec. 2010). "Guidelines For the Diagnosis and Management of Food Allergy in the United States: Report of the NIAID-Sponsored Expert Panel," J. Allergy and Clinical Immunology 126(6):S1-S58.
Buchanan, A.D. et al. (Jan. 2007). "Egg Oral Immunotherapy in Nonanaphylactic Children With Egg Allergy," J. Allergy Clin. Immunol. 119:199-205.
Burks, A.W. (2009). "Early Peanut Consumption: Postpone or Promote?," J. Allergy Clin.Immunol. 123(2):424-425.
Burks, A.W. et al. (Jul. 19, 2012). "Oral Immunotherapy for Treatment of Egg Allergy in Children," N. Engl. J. Med. 3673:233-243.
Burks, W. (2004). "Chapter 17: Food Allergens," Clin. Allergy Immunol. 18:319-337.
Burks, W. (American Academy of Allergy, Asthma, and Immunology National Conference. Orlando, Florida, Mar. 6, 2012). 2012 American Academy of Allergy, Asthma & Immunology Annual Meeting. "Food Allergy" "Oral Immunotherapy for Food Allergens" "Food Allergy Guidelines" "Oral Desensitization in Patients with Food Allergy" Orlando, FL Mar. 2012, 109 pages.
Burks, W. (Apr. 2003). "Peanut Allergy: A Growing Phenomenon," J. Clin. Invest. 111(7):950-952.
Burks, W. (Dec. 2000). "Diagnosis of Allergic Reactions to Food," Pediatr. Ann. 29:744-752.
Burks, W. (Jun. 2003). "Skin Manifestations of Food Allergy," Pediatrics 111(6):1617-1624.
Burks, W. (May 2002). "Current Understanding of Food Allergy," Ann. NY. Acad. Sci. 964:1-12.
Burks, W. et al. (1998). "Review Article Series II: Peanut Allergens," Allergy 53:725-730.

(56) References Cited

OTHER PUBLICATIONS

Burman, J. et al. (2018). "High Arachis Hypogaea Allergen 2 Immunoglobulin E Levels Predict Responses to Exposure to a Small Amount of Peanut Protein," Acta Paediatrica 107:2216, 1 page.

Careri, M. et al. (2007, e-pub. Sep. 27, 2007). "Use of Specific Peptide Biomarkers for Quantitative Confirmation of Hidden Allergenic Peanut Proteins Ara h 2 and Ara h 3/4 for Food Control by Liquid Chromatography-Tandem Mass Spectrometry," Anal. Bioanal. Chem. 389(6):1901-1907.

Carr, T.F. et al. (Feb. 2019). "Longer-Term Safety and Efficacy Measures of AR101 Oral Immunotherapy for Peanut Allergy: Results From a Phase 3 Follow-On Study," Abstract 776: J. Allergy Clin. Immunol. AB256:Abstracts, 1 page.

Chan, C. et al. (2018). "Current Trend in Immunotherapy for Peanut Allergy," Int. Reviews of Immunology 37(6) 279-290.

Chassaigne, H. et al. (2007, e-pub. May 3, 2007). "Proteomics-Based Approach to Detect and Identify Major Allergens in Processed Peanuts by Capillary LC-Q-TOF (MS/MS)," J. of Agricultural and Food Chemistry 55:4461-4473.

Chen, X. et al. (2013, e-pub. Oct. 16, 2012). "Ara h2 and Ara h6 Have Similar Allergenic Activity and Are Substantially Redundant," International Archives of Allergy and Immunology 160:251-258.

Christensen, L.P. et al. (1995). "A Simple HPLC Method for the Isolation and Quantification of the Allergens Tuliposide A and Tulipalin A in Alstroemeria," Contact Dermatitis 32:199-203.

Chu, D. et al. (Jun. 1, 2019, e-pub. Apr. 25, 2019). "Oral Immunotherapy for Peanut Allergy (Pace): A Systematic Review and Meta-Analysis of Efficacy and Safety," Lancet 393:2222-2232.

Clark, A.T. et al. (2009). "Successful Oral Tolerance Induction in Severe Peanut Allergy," Allergy 64:1218-1220.

Clark, A.T. et al. (Aug. 2003). "Interpretation of Tests for Nut Allergy in One ThousandPatients, in Relation to Allergy or Tolerance," Clinical and Experimental Allergy 33(8):1041-1045.

Clinical Trial (Jul. 17, 2018). "Oral Desensitization to Peanut in Peanut-Allergic Children and Adults Using Characterized Peanut Allergen OT (ARC001)," NCT01987817, 7 pages.

Clinical Trial, (Jan. 10, 2019). "PALISADE Follow-on Study (ARC004)," retrieved from https://clinicaltrials.gov/ct2/show/NCT02993107?term=ARC004&rank=1, last visited Feb. 17, 2019, 5 pages.

Curatolo, W. et al. (2011, e-pub. Feb. 18, 2011). "Effects of Food on a Gastrically Degraded Drug: Azithromycin Fast-Dissolving Gelatin and HPMC Capsules," Pharmaceutical Research 28(7):1531-1539.

Davis, C.M. et al. (Feb. 2018). "Peanut Oil Immunotherapy Threshold Dose for Reactivity: What is the Upper Limit?" J. Allergy Clin. Immunol. AB246 Abstract—775, 1 page.

De Oliveira, L.C.L. et al. (2013). "The Value of Specific IgE to Peanut and Its Component Arah 2 in the Diagnosis of Peanut Allergy," J. Allergy Clin. Immunol. 1(4):394-398.

Donelson, S. et al. (Feb. 2020). "Peanut Allergy Burden Survey: Comparison of Responses From Adolescents and Caregivers of Adolescents," J. Allergy Clin. Immunol. Abstract # 468, AB146 Abstracts, 1 page.

Du Toit, G. et al. (May 2018). "Efficacy and Safety of AR101 in Peanut Allergic Patients Aged 4-55: Results from an International Phase 3, Randomised, Double-Blind, Placebo ControlledTrial (PALISADE)," presented at the European Academy of Allergy and Clinical Immunology (EAACI), Munich, Germany, 12 pages.

Dunnglavin, A. et al. (Feb. 23, 2019). "163: APPEAL (Allergy to Peanuts Impacting Emotions and Life): Pan-European Results on Peanut Allergy Impact on Allergic Individuals, Parents and Caregivers," American Academy of Allergy Asthma & Immunology 2019 Annual Meeting, 1 pages.

Epstein-Rigbi, N. et al. (Feb. 2019). "Quality of Life of Food Allergic Patients Before, During, and After Oral Immunotherapy," J of Allergy and Clinical Immunology: In Practice 7(2)429-436.

European Communication Rule 114(2) for European Application No. 14776121.7, dated Oct. 12, 2017, 63 pages.

European Communication Rule 161(2) for European Application No. 1477621.7, dated Oct. 23, 2015, 2 page.

European Communication Rule 70(2) and 70a(2) for European Application No. 14771621.7, dated Sep. 23, 2016, 1 page.

European Communication Rule 94(3) for European Application No. 14776121.7, dated Dec. 19, 2017, 9 pages.

European Communication Rule 94(3) for European Application No. 1477621.7, dated Apr. 26, 2019, 4 page.

European Extended Search Report for European Application No. 14776121.7, dated Aug. 25, 2016, 8 pages.

European Oral Proceedings on for European Application No. 14776121.7, mailed Mar. 27, 2019, 11 page.

Extended European Search Report, dated Apr. 19, 2022, for European Patent Application No. 19849215.9, 14 pages.

Extended European Search Report, dated Mar. 29, 2019, for European Patent Application No. 18213124.3, 15 pages.

Fernández-Rivas, M. et al. (Jun. 6-8, 2020) "PALISADE Follow-On Study (ARC004): Longer-Term Outcomes With AR101 Oral Immunotherapy for Peanut Allergy," Poster 1393, EAACI Digital Congress, 1 page.

Fiocchi, A. et al. (Jul. 2006). "Food Allergy and the Introduction of Solid Foods to Infants: A Consensus Document," Ann. Allergy Asthma Immunol. 97:10-21.

Flinterman, A.E. et al. (2006). "Determination of No-Observed-Adverse-Effect Levels and Eliciting Doses in a Representative Group of Peanut-Sensitized Children," Journal of Allergy and Clinical Immunology 117(2):448-454.

Flinterman, A.E. et al. (2007). "Children With Peanut Allergy Recognized Predominantly Ara h2 and Ara h6, Which Remains Stable Over Time," Clin. Exp. Allergy 37:1221-1228.

Frew, A.J. (2003). "25. Immunotherapy of Allergic Disease," J. Allergy Clin. Immunol. 111(2 Suppl): S712-S719.

Fu, T.J. et al. (Jun. 19, 2013, e-pub. Apr. 8, 2013). "Impacted of Thermal Processing on ELISA Detection of Peanut Allergens," J. Agric. Food. Chem. 61(24): 5649-5658.

Fung, I. et al. (Jan. 8, 2013). "Relating Microarray Component Testing and Reported Food Allergy and Food-Triggered Atopic Dermatitis: A Real-World Analysis," Annals of Allergy, Asthma & Immunology, 110(3):173-177.

Galvin, A.D. et al. (2022). "Summary of Society's Guidelines for Authors," European Academy of Allergy & Clinical Immunology 2022 EAACI Hybrid Congress, 4 pages.

Galvin, A.D. et al. (Apr. 7, 2022). Children and Caregiver Proxy Quality of Life From Peanut Oral Immunotherapy Trials, Manuscript, 48 pages.

Grimshaw, K.E.C. et al. (2015). "Incidence and risk Factors for Food Hypersensitivity in UK Infants: Results From a Birth Cohort Study," Clin Transl Allergy 6:1, 13 pages.

Gugiu, P. et al. (Mar. 18, 2020). "One Ruler to Measure Them All: Combine Data From Multiple Forms," Clinical Outcomes, pp. 1-4.

Hofmann, A.M. et al. (Aug. 2009). "Safety of a Peanut Oral Immunotherapy Protocol in Children With Peanut Allergy," J. Allergy Clin. Immunol. 124:286-291, 14 pages.

Hourihane, J.O. et al. (2019). "OA0166—Improvements in Disease-Specific Quality of Life for Peanut-Allergic Subjects Receiving AR101 Maintenance Therapy," European Journal of Allergy and Clinical Immunology, Abstract, 1 page.

Hourihane, J.O. et al. (Jun. 1997). "Clinical Characteristic of Peanut Allergy," Clinical and Experimental Allergy 27 (6):634-639.

Hourihane, J.O. et al. (Sep. 30-Oct. 2, 2018) "Abstract OP.091: Efficacy and Safety of AR101: Results of the Phase 3 Peanut Allergy Oral Immunotherapy Study for Desensitization (PALISADE) Trial," Abstracts, 2018 Annual Meeting of the British Society for Allergy and Clinical Immunology, 121 pages.

International Preliminary Report of Patentability, issued Nov. 16, 2021, for PCT Application No. PCT/US2020/032179, filed May 8, 2020, 8 pages.

International Preliminary Report on Patentability of PCT Application PCT/US2014/024405, issued Mar. 9, 2015, filed on Mar. 12, 2014, 40 pages.

International Preliminary Report on Patentability Search Report for PCT Application PCT/US2014/024401, issued Sep. 15, 2015, filed Mar. 12, 2014 10 pages.

(56) References Cited

OTHER PUBLICATIONS

International Preliminary Report on Patentability Search Report for PCT Application PCT/US2018/058777, issued May 5, 2020, filed Nov. 1, 2018, 17 pages.

International Preliminary Report on Patentability, issued Jun. 16, 2021 for PCT Application PCT/US2019/067634, filed Dec. 19, 2019, 9 pages.

International Preliminary Report on Patentability, issued Feb. 16, 2021, for PCT Application No. PCT/US2019/046706, filed Aug. 15, 2019, 7 pages.

International Search Report and Written Opinion for PCT Application PCT/US2014/024401, issued Jul. 21, 2014, filed Mar. 12, 2014, 13 pages.

International Search Report and Written Opinion of PCT Application PCT/US2014/024405, mailed Aug. 18, 2014, iled Mar. 12, 2014, 5 pages.

International Search Report and Written Opinion of the International Searching Authority, mailed Feb. 22, 2019, for PCT Application No. PCT/US2018/58777, filed Nov. 1, 2018, 21 pages.

International Search Report and Written Opinion, mailed Aug. 3, 2020, for PCT Application No. PCT/US2020/032179, filed May 8, 2020, 10 pages.

International Search Report and Written Opinion, mailed Jun. 16, 2020, for PCT Application PCT/US2020/23903, filed Mar. 20, 2020, 9 pages.

International Search Report and Written Opinion, mailed Mar. 2, 2020, for PCT Application PCT/US2019/067634, iled Dec. 19, 2019, 11 pages.

International Search Report and Written Opinion, mailed Oct. 29, 2019, for PCT Application No. PCT/US2019/046706, filed Aug. 15, 2019, 13 pages.

Jones, S.M. et al. (2014). "State of the Art on Food Allergen Immunotherapy: Oral, Sublingual, and Epicutaneous," J. Allergy Clin. Immunol. 133(2):318-323.

Jones, S.M. et al. (Aug. 2009). "Clinical Efficacy and Immune Regulation With Peanut Oral Immunotherapy," J. Allergy Clin. Immunol. 124(2):292-300 with Supplemental Information, 106 pages.

Jones, S.M. et al. (Aug. 2009). "Clinical Efficacy and Immune Regulation With Peanut Oral Immunotherapy," J. Allergy Clin. Immunol. 124(2):292-30197, 20 pages.

Jones, S.M. et al. (Mar. 4, 2018). "Efficacy and Safety of AR101 in Peanut Allergy: Results from a Phase 3, Randomized, Double-Blind, Placebo-Controlled Trial (PALISADE)," Late-Breaking Abstract Sessions, AAAAI-WAO Joint Congress, Orlando. The Journal of Allergy and Clinical Immunology 141(2):AB412-AB414. Abstract L6, 14 pages.

Joshi, P.S. et al. (2002). "Interpretation of Commercial Food Ingredient Labels by Parents of Food-Allergic Children," J. Allergy Clin. Immunol. 109(6):1019-1021.

Kapsenberg, M.L. et al. (Jun. 1999). "The Paradigm of Type 1 and Type 2 Antigen-Presenting Cells. Implications for Atopic Allergy," Clin. Exp. Allergy 29(Suppl. 2):33-36.

Kim, E.H., et al. (Mar. 2011). "Sublingual Immunotherapy for Peanut Allergy: Clinical and Immunologic Evidence Of Desensitization," J. Allergy Clin. Immunol. 127(3):640-646, 19 pages.

King, R.M. et al. (2009). "Impact of Peanut Allergy on Quality of Life, Stress and Anxiety in the Family," Allergy, 64 (3):461-468, 31 pages.

Koid, A. et al. (2012). "Purified natural Ara h6: An Important Marker For IgE Response to Peanut," J. Immunology 188 (1001):177. 15 Meeting Abstract Supplemental, 1 page, (Abstract Only).

Koid, A. et al. (Jan. 8, 2014). "Ara h 6 Complements Ara h 2 as an Important Marker For IgE Reactivity to Peanut," J. Agric. Food Chem. 62(1):206-213, 18 pages.

Koppelman et al. (Feb. 19, 1999). "Heat-Induced Conformational Changes of Ara h 1, a Major Peanut Allergen, Do Not Affect Its Allergenic Properties," J. Biol. Chem. 274(8):4770-4777.

Koppelman, S. et al. (2012). "Abstract 1463—The Content of Allergens Arah1, Arah2, Ara h3, and Ara h6 in Different Peanut Cultivars Commonly Consumed in Europe and the USA," Allergy 67(Suppl. 96):548.

Koppelman, S.J. et al. (2001). "Quantification of Major Peanut Allergens Ara h1 and Ara h2 in the Peanut Varieties Runner, Spanish, Virginia, and Valencia, Bred in Different Parts of the World," Allergy 56:132-137.

Koppelman, S.J. et al. (2004). "Relevance of Ara h1, Ara h2, and Ara h3 in Peanut Allergic Patients, as Determined by Immunoglobulin E Western Blotting, Basophil-Histamine Release, and Intracutaneous Testing: Ara h2 Is the Most Important Peanut Allergen," Clin. Exp. Allergy 34:583-590.

Koppleman, S.J. et al. (2010). "Digestion of Peanut Allergens Ara h1, Ara h3 and Ara h6: A Comparative In Vitro Study and Partial Characterization of Digestion-Resistant Peptides," Molecular Nutrition and Food Research 54:1711-1721.

Krieg, A.M. et al. (Apr. 6, 1995). "CpG Motifs in Bacterial DNA Trigger Direct B-Cell Activation," Nature 374:546-549.

Krimpenfort et al. (1988). "Transcription of T Cell Receptor β-Chain Genes Is Controlled by a Downstream Regulatory Element," EMBO J. 7(3):745-750.

Kulis, et al. (Feb. 2012). The 2S Albumin Allergens of Archis Hypogaea, Ara h 2 and Ara h 6, are the Major Elicitors of Anaphylaxis and Can Effectively Desensitize Peanut-Allergic Mice, Clinical & Experimental Allergy: Journal of British Society for Allergy and Clinical Immunology 42(2):326-336, 18 pages.

Lehmann, K. et al. (2006). "Structure and Stability of 2S Albumin-Type Peanut Allergens: Implications for the Severity of Peanut Allergic Reactions," Biochem. J. 395:463-472.

Lehrer, S.B. et al. (1999). "Immunotherapy for Food Allergies. Past, Present, Future," Clin. Rev. Allergy Immunol. 17(3):361-381.

Maloney, J.M. et al. (Jul. 2008, e-pub. May 27, 2008). "The Use of Serum-Specific IgE Measurements for the Diagnosis of Peanut, Tree Nut, and Seed Allergy," Journal of Allergy and Clinical Immunology 122(1):145-151.

Michaud, E. et al. (Apr. 29, 2015). "Peanut Oral Immunotherapy in Adolescents: Study Protocol for a Randomized Controlled Trial," Trials 16(1):197, 6 pages.

Mondoulet et al. (Feb. 21, 2012). "Epicutaneous Immunotherapy (EPIT) Blocks the Allergic Esophago-Gastro-Enteropathy Induced by Sustained Oral Exposure to Peanuts in Sensitized Mice," Plos One 7(2):e31967, 10 pages.

Morishita M. et al. (Oct. 2006). "Is The Oral Route Possible for Peptide and Protein Drug Delivery?" Drug Discovery Today 11(19/20):905-910.

Moutete, H.F. et al. (1995)."Purification of Allergenic Proteins From Peanut for Preparation of the Reactive Solid Phase of a Specific IgE Radioimmunoassay," J. Chromatograph. B. 664:211-217.

Muheem, A. et al. (2014). " A Review on the Strategies for Oral Delivery of Proteins and Peptides and Their Clinical Perspectives," Saudi Pharmaceutical Journal, 16 pages.

Narisety, S.D. et al. (Sep. 2009). "Open-Label Maintenance After Milk Oral Immunotherapy for IgE-Mediated Cow's Milk Allergy," J. Allergy Clin. Immunol. 124(3):610-612, 6 pages.

Nelson, H.S. et al. (1997). "Treatment of Anaphylactic Sensitivity to Peanuts by Immunotherapy With Injections of Aqueous Peanut Extract," J. Allergy Clin. Immunol. 99(6 Pt 1):744-751.

Nicolaou, N. et al. (Jan. 2010). "Allergy or Tolerance in Children Sensitized to Peanut: Prevalence and Differentiation Using Component-Resolved Diagnostics," J. Allergy Clin. Immunol. 125:191-197.

Nowak-Wegrzyn, A. et al. (Feb. 2020). "Peanut Allergy Burden Survey: Impact of Peanut Allergy on Global Quality of Life in Adolescent Patients," J. Allergy Clin. Immunol. Abstract # 466, AB146 Abstracts, 1 page.

Ohayon, J. et al. (Feb. 2020). "Improvements in Self-Reported Disease-Specific Quality of Life Among Peanut-Allergic Subjects Receiving AR101 for 28 or 56 Weeks Beyond the First Year of Treatment," J. Allergy Clin. Immunol. Abstract # 432, AB136 Abstracts, 1 pages.

Oppenheimer, J.J. et al. (1992). "Treatment of Peanut Allergy With Rush Immunotherapy," J. Allergy Clin. Immunol. 90(2):256-262.

(56) References Cited

OTHER PUBLICATIONS

O'Connell. (2012). "Uses of Sieves in the Pharmaceutical Industry and the Increased Demand for Containment," International Pharmaceutical Industry 4(4):88-90.
Pajno, G.B. et al. (2014). "Oral Immunotherapy for Treatment of Immunoglobulin E-Mediated Food Allergy: The Transition to Clinical Practice," Pediatr Allergy Immunol Pulmonol. 27(2):42-50.
Partial Supplementary European Search Report, dated Aug. 3, 2021, for European Patent Application No. 18871949.6, 18 pages.
Peeters, K.A.B.M. et al. (2007). "Does Skin Prick Test Reactivity to Purified Allergens Correlate With Clinical Severity of Peanut Allergy?" Clinical and Experimental Allergy 37:108-115.
Pele, M. (2010). "Peanut Allergens," Romanian Biotechnological Letters 15(2):5204-5212.
Pingali, K. et al. (May 16, 2011, e-pub. Feb. 26, 2011). "Mixing Order of Glidant and Lubricant—Influence on Powder and Table Properties," Int. J. Pharm. 409:269-277, 22 pages.
Pisetsky, D.S. (Oct. 1996). "Immune Activation by Bacterial DNA: A New Genetic Code," Immunity 5:303-310.
Podczek, F. et al. (1999). "The Filling of Granules Into Hard Gelatin Capsules," International Journal of Pharmaceutics 188(1):59-69.
Poms, R.E. et al. (2004). "Effect of Roasting History and Buffer Composition on Peanut Protein Extraction Efficiency," Mol. Nutr. Food Res 48:459-464.
Porterfield, H.S. et al. (Jul. 2009). "Effector Activity of Peanut Allergens: A Critical Role for Ara h2, Ara h6 and Their Variants," Clin. Exp. Allergy 39(7):1099-1108, 19 pages.
Pre-interview First Office Action for U.S. Appl. No. 14/207,165, mailed Mar. 12, 2015, 4 pages.
Prescott, K. et al. (Mar. 2-5, 2018). "Exploration of Non-Daily Maintenance Dosing Regimens in Peanut Oral Immunotherapy," Scientific Abstract Sessions, AAAAI-WAO Joint Congress, Orlando. The Journal of Allergy and Clinical Immunology Abstract 772, 141(2):AB294-AB361, 1 page.
Project Code (2020). "Devising and Testing a Scoring Algorithm for the Food Allergy Quality of Life Questionnaire (FAQLQ) Across Multiple Forms," Clinical Outcomes pp. 1-3.
Publication Information for Burman, J. et al. (2018). "High Arachis Hypogaea Allergen 2 Immunoglobulin E Levels Predict Responses to Exposure to a Small Amount of Peanut Protein," Acta Paediatrica 107:2216, retrieved from Internet https://onlinelibrary.wiley.com/doi/abs/10.1111/apa.14511, last visited Feb. 7, 2021.
Rancé, F. et al. (Jun. 2002). "Improved Screening for Peanut Allergy by the Combined Use of Skin Prick Tests and Specific IgE Assays," Journal of Allergy and Clinical Immunology 109(6):1027-1033.
Response to Communication Rule 161(1) for European Application No. 14776121.7, dated Apr. 29, 2016, 12 pages.
Response to Communication Rule 70a(2) for European Application No. 14771621.7, dated Mar. 26, 2017, 13 pages.
Roberts, G. et al. (Jun. 2005). "Diagnosing Peanut Allergy With Skin Prick and Specific IgE Testing," J. Allergy Clin. Immunol. 115:1291-1296.
Salvilla, S.A. et al. (May 16, 2014). "Disease-Specific Health-Related Quality of Life Instruments for IgE-Mediated Food Allergy," Allergy 69:834-844.
Sampson, H. A. et al. (2011). "A Phase II, Randomized, Double Blind, Parallel Group, Placebo Controlled Oral Food Challenge Trial of Xolair (omalizumab) in Peanut Allergy," J. Allergy Clin. Immunol. 127(5):1309-1310.
Sampson, H.A. et al. (1997). "Clinical Aspects of Allergic Disease: Relationship Between Food-Specific IgE Concentrations and the Risk of Positive Food Challenges in Children and Adolescents," J. Allergy Clin. Immunol. 100 (4):444-451.
Sampson, H.A. et al. (2005). "Symposium on the Definition and Management of Anaphylaxis: Summary Report," J. Allergy Clin. Immunol. 115(3):584-591.
Santos, A.F. et al. (Sep. 2014). "Food, Drug, Insect Sting Allergy, and Anaphylaxis: Basophil Activation Test Discriminates Between Allergy and Tolerance in Peanut-Sensitized Children," J. Allergy Clin. Immunol. 134:645-652.
Schmitt, D.A. et al. (2010, e-pub. Dec. 22, 2009). "Processing Can Alter the Properties of Peanut Extract Preparations," J. Agric. Food Chem. 58:1138-1143.
Schneider, L.C. et al. (2013, e-pub. Oct. 28, 2013). "A Pilot Study of Omalizumab to Facilitate Rapid Oral Desensitization in High-Risk Peanut-Allergic Patients," J. Allergy Clin. Immunol. 132:1368-1374.
Schurlock, A.M. et al. (Nov. 1, 2004). "Peanut Allergenicity," Annals of Allergy, Asthma & Immunology 93(5): S12-S18.
Secrist, H. et al. (Mar. 1995). "Interleukin 4 Production by CD4+ T Cells From Allergic Individuals Is Modulated by Antigen Concentration and Antigen-Presenting Cell Type," J. Exp. Med. 181(3):1081-1089.
Sen, M. et al. (2002). "Protein Structure Plays a Critical Role in Peanut Allergen Stability and May Determine Immunodominant IgE-Binding Epitopes," The Journal of Immunology 169:882-887.
Sher, E. et al. (May 2018). "Efficacy and Safety of AR101 in Peanut Allergy: Results from a Phase 3, Randomized, Double-Blind Placebo Controlled Trial (PALISDAE)," presented at the Eastern Allergy Conference (EAC), Palm Beach, Florida, 1 page.
Shreffler, W.G. et al. (Apr. 2004). "Microarray immunoassay: Association of Clinical History, in vitro IgE Function, and Heterogeneity of Allergenic Peanut Epitopes," J. Allergy Clin. Immunol. 113(4):776-782.
Sicherer, S.H. (2011, e-pub. Jan. 13, 2011). "Epidemiology of Food Allergy," J. Allergy Clin. Immunol. 127 (3):594-602.
Sicherer, S.H. (Nov. 1999). "Food Allergy: When and How to Perform Oral Food Challenges," Pediatr. Allergy Immunol. 10(4):226-234.
Sicherer, S.H. et al. (Feb. 2014, e-pub. Dec. 31, 2013). "Food Allergy: Epidemiology, Pathogenesis, Diagnosis, and Treatment," J. Allergy Clin. Immunol. 133:291-307.
Sicherer, S.H. et al. (Jul. 1998). "Clinical Features of Acute Allergic Reactions to Peanut and Tree Nuts in Children," Pediatrics 102(1):1-6.
Sicherer, S.H. et al. (May 2010). "Immunologic features of Infants With Milk or Egg Allergy Enrolled in an Observational Study (Consortium of Food Allergy Research) of Food Allergy)," J. Allergy Clin. Immunol. 125:1077-1083, 14 pages.
Singh, H. et al. (Oct. 2011). "Developing RP-HPLC Method for Detection of Peanut Allergens," in AACC International Annual Meeting, Oct. 16-19, 2011. Retrieved from the Internet http://www.aaccnet.org/meetings/Documents/2011Abstracts/p11ma199.htm, last visited Feb. 17, 2016, 1 page. (Abstract Only).
Skolnick, H.S. et al. (Feb. 2001). "Food and Drug Reactions and Anaphylaxis: The Natural History of Peanut Allergy," J. Allergy Clin. Immunol. 107(2):367-374.
Skripak, J.M. et al. (2009). "Mammalian Milk Allergy: Avoidance Strategies and Oral Desensitization," Curr. Opin. Allergy Clin. Immunol. 9:259-264.
Skripak, J.M. et al. (Dec. 2008). "A Randomized, Double-Blind, Placebo-Controlled Study of Milk Oral Immunotherapy for Cow's Milk Allergy," J. Allergy Clin Immunol. 122(6): 1154-1160, 20 pages.
Summons to Attend Oral Proceeding Pursuant to Rule 115(1) EPC, mailed Oct. 25, 2018, for European Patent Application No. 14776121.7, 7 pages.
Tan, S.B. et al. (1990). "Powder Flowability as an Indication of Capsule Filling Performance," International Journal of Pharmaceutics 61(1-2):145-156.
Thyagarajan, A. et al. (Feb. 2009). "Basophil Suppression in Peanut Allergic Subjects undergoing Peanut Oral Immunotherapy (OIT)," Journal of Allergy and Clinical Immunology 123:S214-S214, (Abstract Only).
Tilles, S. et al. (Mar. 2020). "Peanut Allergy Burden Survey: Correlates of Food Allergy Quality of Life Questionnaire—Teen Form Scores," J. Allergy Clin. Immunol. 145(2): Abstract # 469, AB147 Abstracts, 1 page.
Van Der Velde, J.L. et al. (May 2010). "Development, Validity and Reliability of the Food Allergy Independent Measure (FAIM)," Allergy 65(5)630-635.
Van Der Zee, T. et al. (Nov. 2011). "The Eliciting Dose of Peanut in Double-Blind, Placebo-Controlled Food Challenges Decreases

(56) References Cited

OTHER PUBLICATIONS

With Increasing Age and Specific IgE Level in Children and Young Adults," J. Allergy Clin. Immunol. 128(5):1031-1036.
Van Veen, W.J. et al. (2013). "Predictive Value of Specific IgE for Clinical Peanut Allergy in Children: Relationship With Eczema, Asthma, and Setting (Primary or Secondary Care)," Clinical and Translational Allergy 3:34, 7 pages.
Vander Leek, T.K. et al. (Dec. 2000). "The Natural History of Peanut Allergy in Young Children and its Association With Serum Peanut-Specific IgE," J. Pediatr. 137(6):749-755.
Varshney, P. et al. (2009, e-pub. Nov. 13, 2009). "Adverse Reactions During Peanut Oral Immunotherapy Home Dosing," J. Allergy Clin. Immunol. 124(6):1351-1352, 5 pages.
Varshney, P. et al. (Mar. 2011). A Randomized Controlled Study of Peanut Oral Immunotherapy: Clinical Desensitization and Modulation of the Allergic Response, J. Allergy and Clinical Immunology 127(3):654-660.
Vereda, A. et al. (Sep. 30-Oct. 5, 2018). "Abstract 139: Efficacy and Safety of AR101: Results of the Phase 3 Peanut Allergy Oral Immunotherapy Study for Desensitization(PALISADE) Trial," Abstract: Allergy Across the Life Course—From Origins Towards Prevention, 32nd Symposium of the Collegium International Allergologium, 84 pages.
Vickery, B.P. et al. (Jan. 2013). "Peanut Oral Immunotherapy Modifies IgE and IgG4 Responses to Major Peanut Allergens," J. Allergy Clin. Immunol. 131(1):128-134.e3, 16 pages.
Vierk, K., et al. (Jun. 2002). "Recalls of Foods Containing Undeclared Allergens Reported to the US Food and Drug Administration, Fiscal Year 1999," J. Allergy Clin. Immunol. 109(6):1022-1026.
Virkud, Y.V. et al. (Mar. 2017). "Novel Baseline Predictors of Adverse Events During Oral Immunotherapy in Children With Peanut Allergy," J. Allergy Clin. Immunol 139(3):882-888.

Wainstein, B.K. et al. (Jun. 2010). "Prediction of Anaphylazis During Peanut Food Challenge: Usefulness of the Peanut Skin Prick Test (SPT) and Specific IgE Level," Pediatr. Allergy Immunol. 21(4)(Pt. 1):603-611.
Wang, J. et al. (Feb. 2019). "Impact of Peanut Allergy on Quality of Life: Baseline Results from PALISADE, a Phase 3, Double-Blind, Placebo-Controlled Trial for AR101 Oral Immunotherapy," J. Allergy Clin. Immunol. 143(2):468, Abstracts AB155, 1 page.
Wang, J. et al. (Mar. 2011). "Food Allergy," J. Clinical Investigations 121(3):827-835.
Wensing, M. et al. (Dec. 2002). "The Distribution of Individual Threshold Doses Eliciting Allergic Reactions in a Population With Peanut Allergy," J Allergy Clin Immunol. 100(6):915-920.
Wilson, D.R. et al. (2005). "Sublingual Immunotherapy for Allergic Rhinitis: Systematic Review and Meta-Analysis," Allergy 60(1):4-12.
Yamamoto, S. et al. (1992). "DNA From Bacteria, but Not From Vertebrates, Induces Interferons, Activates Natural Killer Cells and Inhibits Tumor Growth," Microbiol. Immunol. 36(9):983-997.
Zhuang, Y. et al. (Sep. 5, 2012). "Redefining the Major Peanut Allergens," Immunologic Research 55 (1-3):125-134.
Zimmermann, S. et al. (1998). "Cutting Edge: CpG Oligodeoxynucleotides Trigger Protective and Curative Th1 Responses in Lethal Murine Leishmaniasis," J. Immunol. 160:3627-3630.
Examination report issued in corresponding Australian Application No. 2019401214, dated Sep. 4, 2024, 3 pages.
Tang, et al., "Administration of a probiotic with peanut oral immunotherapy: A randomized trial", Journal of Allergy and Clinical Immunology, 2015, vol. 135, No. 3, pp. 737-744.e8, DOI: 10.1016/j.jaci.2014.11.034.

* cited by examiner

Guidelines for Missed Consecutive Doses During Up-Dosing

| Consecutive Missed Doses | Action |
|---|---|
| 1 to 2 consecutive doses | Resume up-dosing at the same dose level without medical supervision |
| 3 to 4 consecutive doses | Resume up-dosing at the same dose level under medical supervision |
| 5 to 7 consecutive doses | Resume up-dosing under medical supervision at a dose reduction of 50% or more compared to the last administered dose |
| 8 to 14 consecutive doses | Resume up-dosing under medical supervision at a dose reduction of 75% or more compared to the last administered dose |
| Greater than 14 consecutive doses | Restart up-dosing at the lowest initial up-dosing dose |

FIG. 2

Guidelines for Missed Consecutive Doses During Maintenance

| Consecutive Missed Doses | Action |
|---|---|
| 1 to 2 consecutive doses | Resume dosing at the same dose level without medical supervision |
| 3 to 4 consecutive doses | Resume dosing at the same dose level under medical supervision |
| 5 to 7 consecutive doses | End maintenance and restart up-dosing under medical supervision at a dose reduction of 50% or more compared to the last administered dose |
| 8 to 14 consecutive doses | End maintenance and restart up-dosing under medical supervision at a dose reduction of 50% or more compared to the last administered dose |
| Greater than 14 consecutive doses | End maintenance and restart up-dosing at the lowest initial up-dosing dose |

FIG. 3

PEANUT ORAL IMMUNOTHERAPY DOSING SCHEDULE FOR MISSED DOSES

CROSS-REFERENCE TO RELATED APPLICATION

This application claims priority benefit of U.S. Provisional Application No. 62/783,102, filed Dec. 20, 2018, the contents of which are incorporated by reference herein in its entirety.

FIELD OF THE INVENTION

Described herein are methods for continuing an oral immunotherapy for the treatment of a peanut allergy after the patient being treated has missed one or more consecutive doses in a dosing schedule.

BACKGROUND OF THE INVENTION

Peanut allergy is an allergic hypersensitivity reaction of the immune system to peanut protein. Peanut allergy often develops in childhood and is usually a lifelong affliction. Allergic reactions to peanut can be severe and life threatening, and are a major source of severe food-induced anaphylaxis.

Until recently, the standard of care for treating peanut allergy included dietary elimination and avoidance of peanuts, education on the signs of anaphylaxis, and administration of injectable epinephrine in response to severe allergic reactions with dietary exposure to peanut protein. However, accidental ingestion of peanuts is common, due to difficulty in interpreting food labels and the presence of undeclared ingredients in unlabeled food. Oral immunotherapy (OIT) is a promising new treatment for peanut allergy. See, for example, Bird et al., *Efficacy and Safety of AR101 in Oral Immunotherapy for Peanut Allergy: Results of ARC001; a randomized Double-Blind, Placebo-Controlled Phase 2 Clinical Trial*, J. Allergy Clin. Immunol. Pract., vol. 6, no. 2, p. 476-485 (2018) and Vickery et al., *AR101 Oral Immunotherapy for Peanut Allergy*, N. Engl. J. Med. 2018; 379:1991-2001. Peanut OIT includes exposing patients to gradually increasing doses of peanut protein to induce desensitization, which is intended to reduce the risk of anaphylaxis after accidental exposure to peanut.

Although peanut OIT has been shown to be effective at inducing a desensitized state in many patients, the safety of the therapy depends, in part, on the adherence of the patient to the oral immunotherapy schedule. Deviation from the dosing schedule at any time in the oral immunotherapy presents a safety risk and may reduce the efficacy of the immunotherapy. Treated patients may occasionally miss one or more doses of the up-dosing phase or the maintenance phase of an immunotherapy, due to voluntary noncompliance, inadvertent noncompliance, or adverse reactions. Oral immunotherapy methods that allow patients to safely and effectively continue an oral immunotherapy after one or more consecutive missed doses are desired.

SUMMARY OF THE INVENTION

Described herein are methods of continuing an oral immunotherapy for the treatment of a peanut allergy in a patient after missing a scheduled administration of one or more consecutive doses of a pharmaceutical composition comprising peanut protein, and kits comprising a dose of a pharmaceutical composition comprising peanut protein and instructions for use according to the method of continuing the oral immunotherapy. The oral immunotherapy comprises (i) an up-dosing phase comprising orally administering to the patient a series of escalating doses of the pharmaceutical composition on a daily basis, wherein a given dose is administered to the patient for at least a predetermined period of time before the dose is escalated, and (ii) a maintenance phase comprising orally administering to the patient a plurality of maintenance doses of the pharmaceutical composition.

In some embodiments, the method of continuing an oral immunotherapy for the treatment of a peanut allergy in a patient after missing a scheduled administration of one or more consecutive doses of a pharmaceutical composition comprising peanut protein comprises orally administering to the patient a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed, (i) the dose administered to the patient is the same as the most recently administered dose and the dose is administered to the patient under medical supervision, or (ii) the dose administered to the patient is reduced compared to the most recently administered dose; (3) if five to fourteen consecutive doses are missed, the dose administered to the patient is reduced by about 50% or more; and (4) if more than fourteen consecutive doses are missed, the dose administered to the patient is an initial dose of the up-dosing phase.

In some embodiments, one or two consecutive doses are missed, and the dose administered to the patient is the same as the most recently administered dose. In some embodiments, the dose is administered to the patient without medical supervision. In some embodiments, the dose is administered to the patient under medical supervision.

In some embodiments, three or four consecutive doses are missed, and the dose administered to the patient is reduced compared to the most recently administered dose. In some embodiments, the dose administered to the patient is reduced by 25% or more. In some embodiments, the dose administered to the patient is reduced by 50% or more. In some embodiments, the dose is administered to the patient under medical supervision. In some embodiments, the dose is administered to the patient without medical supervision.

In some embodiments, three or four consecutive doses are missed, the dose administered to the patient is the same as the most recently administered dose, and the dose is administered to the patient under medical supervision.

In some embodiments, five to fourteen consecutive doses are missed, and the dose administered to the patient is reduced by about 50% or more.

In some embodiments, if five to seven consecutive doses are missed, the dose administered to the patient is reduced by about 50% or more compared to the most recently administered dose. In some embodiments, five to seven consecutive doses are missed, and the dose administered to the patient is reduced by about 50% or more compared to the most recently administered dose.

In some embodiment, if eight to fourteen consecutive doses are missed during the up-dosing phase, the dose administered to the patient is reduced by about 75% or more. In some embodiments, eight to fourteen consecutive doses are missed during the up-dosing phase, and the dose administered to the patient is reduced by about 75% or more compared to the most recently administered dose.

In some embodiments, if eight to fourteen consecutive doses are missed during the maintenance phase, the dose administered to the patient is reduced by about 50% or more compared to the most recently administered dose. In some embodiments, eight to fourteen consecutive doses are missed during the maintenance phase, and the dose administered to the patient is reduced by about 50% or more compared to the most recently administered dose.

In some embodiments, more than fourteen consecutive doses are missed, and the dose administered to the patient is the initial dose of the up-dosing phase. In some embodiments, the initial dose of the up-dosing phase is about 1 mg to about 6 mg of peanut protein. In some embodiments, the initial dose of the up-dosing phase is about 3 mg of peanut protein Also described herein is a method of continuing an oral immunotherapy for the treatment of a peanut allergy in a patient after missing a scheduled administration of one or more consecutive doses of a pharmaceutical composition comprising peanut protein, comprising orally administering to the patient a dose of the pharmaceutical composition after missing the scheduled one or more consecutive doses, wherein: (1) if one to x consecutive doses are missed, the dose administered to the patient is the same as the most recently administered dose; (2) if (x+1) to y consecutive doses are missed, (i) the dose administered to the patient is the same as the most recently administered dose and the dose is administered to the patient under medical supervision, or (ii) the dose administered to the patient is reduced compared to the most recently administered dose; (3) if (y+1) to z consecutive doses are missed, the dose administered to the patient is reduced by about 25% or more; and (4) if more than z consecutive doses are missed, the dose administered to the patient is an initial dose of the up-dosing phase; wherein x, y, and z are positive integers, and x<y<z; x is 1, 2, 3, 4, or 5; y is 2, 3, 4, 5, 6, or 7; and z is 3, 4, 5, 6, 7, 8, 9, 10, 11, 12, 13, 14, 15, 16, 17, 18, 19, 20, or 21.

In some embodiments, one to x consecutive doses are missed, and the dose administered to the patient is the same as the most recently administered dose. In some embodiments, the dose is administered to the patient without medical supervision. In some embodiments, the dose is administered to the patient under medical supervision.

In some embodiments, (x+1) to y consecutive doses are missed, and the dose administered to the patient is reduced compared to the most recently administered dose. In some embodiments, the dose administered to the patient is reduced by 50% or more. In some embodiments, the dose administered to the patient is reduced by 75% or more. In some embodiments, the dose is administered to the patient under medical supervision. In some embodiments, the dose is administered to the patient without medical supervision.

In some embodiments, (x+1) to y consecutive doses are missed, the dose administered to the patient is the same as the most recently administered dose, and the dose is administered to the patient under medical supervision. In some embodiments, if (y+1) to z consecutive doses are missed, the dose administered to the patient is reduced by about 50% or more. In some embodiments, if (y+1) to z consecutive doses are missed, the dose administered to the patient is reduced by about 75% or more. In some embodiments, (y+1) to z consecutive doses are missed, and the dose administered to the patient is reduced by about 50% or more. In some embodiments, (y+1) to z consecutive doses are missed, and the dose administered to the patient is reduced by a greater amount if the doses were missed during the up-dosing phase compared to if the same number of doses were missed during the maintenance phase. In some embodiments, if (y+1) to z consecutive doses are missed, the dose administered to the patient is reduced by a greater amount if the doses were missed during the up-dosing phase compared to if the same number of doses were missed during the maintenance phase.

In some embodiments, more than z consecutive doses are missed, and the dose administered to the patient is the initial dose of the up-dosing phase. In some embodiments, the initial dose of the up-dosing phase about 1 mg to about 6 mg of peanut protein. In some embodiments, the initial dose of the up-dosing phase is about 3 mg of peanut protein In some embodiments of the above methods, the missed one or more consecutive doses were scheduled during the up-dosing phase. In some embodiments of the above methods, the missed one or more consecutive doses were scheduled during the maintenance phase.

In some embodiments of the above methods, the pharmaceutical composition comprises defatted peanut flour.

In some embodiments of the above methods, the maintenance doses of the pharmaceutical composition comprise about 200 mg to about 1000 mg peanut protein. In some embodiments, the maintenance doses of the pharmaceutical composition comprise about 300 mg peanut protein.

In some embodiments of the above methods, the series of escalating doses of the pharmaceutical composition administered during the up-dosing phase comprises 5 to 15 different dose levels. In some embodiments, the series of escalating doses administered during the up-dosing phase comprises 11 different dose levels.

In some embodiments of the above methods, the series of escalating doses administered during the up-dosing phase comprises doses of about 1 mg to about 1000 mg peanut protein. In some embodiments, the series of escalating doses administered during the up-dosing phase comprises doses of about 3 mg to about 300 mg peanut protein.

In some embodiments of the above methods, the series of escalating doses administered during the up-dosing phase comprises doses of about 3 mg peanut protein, about 6 mg peanut protein, about 12 mg peanut protein, about 20 mg peanut protein, about 40 mg peanut protein, about 80 mg peanut protein, about 120 mg peanut protein, about 160 mg peanut protein, about 200 mg peanut protein, about 240 mg peanut protein, and about 300 mg peanut protein.

In some embodiments of the above methods, a given dose is administered to the patient for at least one week during the up-dosing phase before the dose is escalated. In some embodiments, a given dose is administered to the patient for at least two weeks during the up-dosing phase before the dose is escalated.

Also described herein is a kit comprising a plurality of doses of a pharmaceutical composition comprising peanut protein, and instructions according to any one of the above methods. In some embodiments, the plurality of pharmaceutical doses comprise the same amount of peanut protein. In some embodiments, the plurality of pharmaceutical doses comprises about 10 to about 45 doses of peanut protein. In some embodiments, the plurality of pharmaceutical doses comprises about 15 doses. In some embodiments, the plurality of pharmaceutical doses comprises pharmaceutical doses for administration during the up-dosing phase. In some embodiments, the plurality of pharmaceutical doses comprises about 30 doses. In some embodiments, the plurality of pharmaceutical doses comprises pharmaceutical doses for administration during the maintenance phase.

Further described herein is a pharmaceutical composition comprising peanut protein for use in a method of continuing an oral immunotherapy according to any one of the above methods.

Further described herein is a pharmaceutical composition comprising peanut protein for the manufacture of a medicament for a method of continuing an oral immunotherapy according to any one of the above methods.

BRIEF DESCRIPTION OF THE DRAWINGS

FIG. 2 shows an exemplary set of guidelines for actions to take after a patient misses a set range of consecutive doses during the up-dosing phase of an oral immunotherapy.

FIG. 3 shows an exemplary set of guidelines for actions to take after a patient misses a set range of consecutive doses during the maintenance phase of an oral immunotherapy.

DETAILED DESCRIPTION OF THE INVENTION

Figure 1:
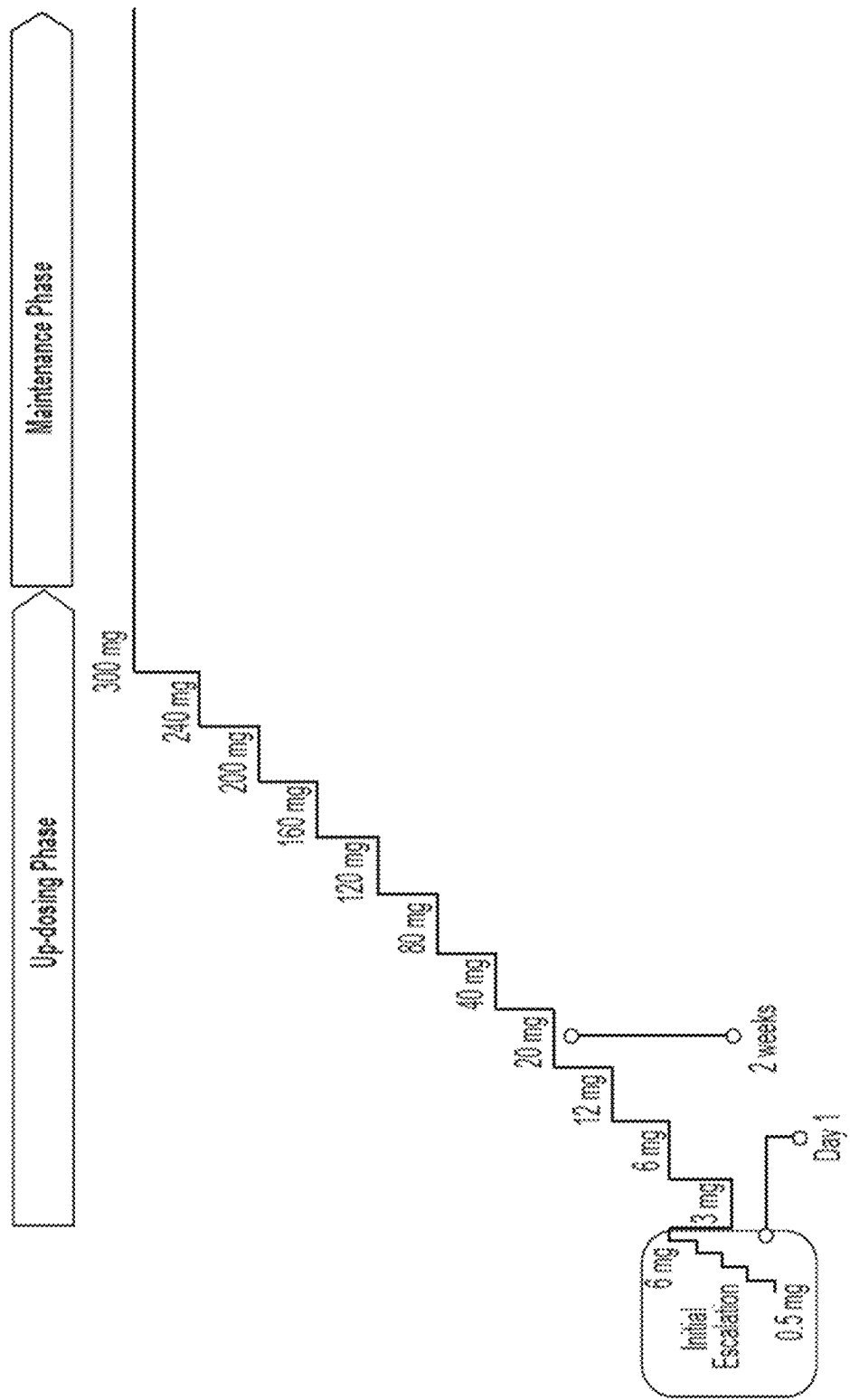
FIG. 1 shows an exemplary oral immunotherapy dosing schedule for treating a peanut allergy, including an option initial escalation phase, an exemplary up-dosing phase, and an exemplary maintenance phase. The schedule may be adjusted depending on the patient's response to the administered pharmaceutical composition.

Described herein are methods of continuing an oral immunotherapy for the treatment of a peanut allergy in a patient after missing a scheduled oral administration of one or more consecutive doses of a pharmaceutical composition comprising peanut protein, the oral immunotherapy comprising (i) an up-dosing phase comprising orally administering to the patient a series of escalating doses of the pharmaceutical composition on a daily basis, wherein a given dose is administered to the patient for at least a predetermined period of time before the dose is escalated, and (ii) a maintenance phase comprising orally administering to the patient a plurality of maintenance doses of the pharmaceutical composition, the method comprising orally administering to the patient a dose of the pharmaceutical composition after missing the scheduled one or more consecutive doses.

Oral immunotherapy is a method of inducing desensitization to an allergen in a patient by regular exposure of the patient to increasing doses of the allergen. For peanut allergy, protocols for OIT typically involve an up-dosing phase (also called a build-up phase) and a maintenance phase. Preferably, the OIT further includes an initial escalation phase, although this phase is optional and not required for treatment. The initial escalation phase involves exposure to small doses of peanut protein under clinical supervision to determine the sensitivity of the patient to the peanut protein. This initial escalation phase generally occurs over the course of several (e.g., three or more) hours to two days. These small doses are increased until the patient reaches a goal dose or a highest tolerated dose for the initial escalation phase. The patient then usually begins an up-dosing phase, with regular consultation with a medical caregiver, usually beginning with the highest tolerated dose administered in the initial escalation phase or a slightly lower dose, and escalating through a series of doses. Additionally, peanut OIT includes a maintenance phase involving the long-term administration of peanut protein. The primary goal of oral immunotherapy is establishing a desensitized state, wherein the patient being treated is less likely to suffer a severe or life-threatening allergic reaction upon accidental exposure to peanut protein.

During the course of the up-dosing phase or maintenance phase a patient may miss one or more consecutive doses. Any missed dose at any time in the oral immunotherapy presents a safety risk and may reduce efficacy of the immunotherapy. Patients may occasionally miss one or more doses of the up-dosing phase or the maintenance phase of an immunotherapy. Doses may be missed due to: voluntary noncompliance, including poor dose-taking habit or forgetfulness on the part of the patient; inadvertent noncompliance, including financial difficulty in obtaining drug product, treatment-unrelated life events, incapacitation, or confusion; and/or adverse events including allergic reactions of any grade or treatment-unrelated adverse events of any grade. The improved peanut oral immunotherapies described herein allow a patient to safely and effectively continue an oral immunotherapy after missing one or more consecutive doses.

Definitions

As used herein, the singular forms "a," "an," and "the" include the plural references unless the context clearly dictates otherwise.

Reference to "about" a value or parameter herein includes (and describes) variations that are directed to that value or parameter per se. For example, description referring to "about X" includes description of "X".

The term "desensitized" is used herein to refer to an increased allergic reaction threshold to a food allergen by a patient as a result of an oral immunotherapy for the food allergen. Desensitization to a food allergen can be tested using methods known in the art, including an oral food challenge. Desensitization may be partial, wherein the patient tolerates an increased amount of the food allergen compared to prior to treatment, but still reacts to higher doses of the food allergen; or the desensitization may be complete, wherein the patient tolerates all tested doses of the food allergen.

The terms "effective," "efficacy," or "effectiveness" are used herein to refer to the ability of a therapy to induce immune modulation, such as desensitization, or sustain a desired immune state, such as a desensitized state, unless otherwise indicated.

As used herein, "maintenance phase" refers to a phase of a peanut protein oral immunotherapy that includes administration of peanut protein (i.e., a maintenance dose) to the patient, and occurs after completion of the up-dosing phase.

As used herein, a "mild allergic adverse event" refers to an observed or experienced OIT-treatment-related allergic adverse event associated with transient discomfort, requires no immediate medical intervention or requires only an oral administration of anti-allergic medication, and does not substantially interfere with daily activities.

As used herein, a "missed dose" is a dose scheduled to be taken on a calendar day that is not administered to the patient on the scheduled calendar day. A missed dose may be intentionally missed or unintentionally missed.

As used herein, a "moderate allergic adverse event" refers to an observed or experienced OIT-treatment-related allergic adverse event that is more severe than a mild allergic adverse event but not rise to the severity of a severe allergic adverse event.

As used herein, the phrase "severe allergic adverse event" refers to an observed or experienced OIT-treatment-related allergic adverse event that is life-threatening; results in loss of bowel control, cyanosis, hemoglobin saturation less than 92%, respiratory arrest, hypotension (blood pressure of less than 70 mm Hg for a patient less than 1 year of age, blood pressure of less than (70 mm Hg+(2×age)) for a patient 1-10 years of age, or blood pressure less than 90 mmHg for a patient 11 years of age or older), collapse, dysrhythmia, cardiac arrest, or loss of consciousness; results in hospitalization for reasons other than observation; or results in death of the patient.

The terms "patient" is used to describe a human being treated by oral immunotherapy.

A patient "tolerates" a dose when the dose is administered to the patient and fully consumed by the patient without any moderate or severe allergic adverse event in response to the dose. A patient is considered to tolerate the dose even if a mild allergic adverse event is observed or experienced. A "highest tolerated dose" is the maximum dose administered to the patient during an oral food challenge that is tolerated by the patient without any moderate or severe allergic adverse event. A "cumulative tolerated dose" is the sum of doses administered to the patient during an oral food challenge up to and including the highest tolerated dose, without any moderate or severe allergic adverse event.

The terms "treat," "treating," and "treatment" are used synonymously herein to refer to any action providing a benefit to a patient afflicted with a disease state or condition, including improvement in the condition through lessening, inhibition, suppression, or elimination of at least one symptom; delay in progression of the disease; delay in recurrence of the disease; inhibition of the disease; or partially or fully reducing a response or reaction to an allergen.

As used herein, a patient is "under medical supervision" during the administration of a dose when the patient is in a setting in which a medical professional is available to provide immediate medical intervention in the event of a treatment-related adverse event due to administration of the dose.

An "up-dosing phase" refers to a phase of an oral immunotherapy characterized by a series of increasing food allergen doses, beginning with administration of a dose of food allergen lower than the highest dose administered to the patient during the oral immunotherapy, and ending when the highest dose administered to the patient during the oral immunotherapy is achieved.

It is understood that aspects and variations of the invention described herein include "consisting" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

The section headings used herein are for organization purposes only and are not to be construed as limiting the patient matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The disclosures of all publications, patents, and patent applications referred to herein are each hereby incorporated by reference in their entireties. To the extent that any reference incorporated by reference conflicts with the instant disclosure, the instant disclosure shall control.

Peanut Oral Immunotherapy

A patient having a peanut allergy can be treated for the peanut allergy by administering a series of doses of a peanut protein composition, according to a dosing schedule, to the patient during the course of an oral immunotherapy, thereby desensitizing the patient to the peanut allergy. The oral immunotherapies described herein are multi-phasic, and include at least an up-dosing phase and a maintenance phase. Optionally, the oral immunotherapy includes an initial escalation phase preceding the up-dosing phase.

During a normal oral immunotherapy schedule, the doses of peanut protein composition administered to the patient during the up-dosing phase are periodically increased until a target dose is reached. For example, during the up-dosing phase, the patient is administered the same dose of peanut protein composition on a daily basis for a period of time (for example, 1, 2, 3, 4 or more weeks), before the dose is increased. Following the up-dosing phase, a maintenance dose is administered to the patient, which maintains the patient in a state of desensitization to the peanut protein. The duration of the therapy, for example the duration of the up-dosing and/or maintenance phase may vary between patients depending on the age, health conditions, the severity of the peanut allergy, tolerability of the pharmaceutical product, and/or complicating co-morbid diseases or conditions, among other factors. The amount of the doses of the peanut protein composition administered in the up-dosing and maintenance phases can be adjusted as necessary based on the judgment of a patient's medical caregiver and/or the needs of the patient.

Although preferred treatment includes strict adherence to a dosing schedule (for example, daily administration during the up-dosing phase and/or maintenance phase), occasionally the patient will miss one or more consecutive doses. Missing multiple consecutive doses can lead to significant risk upon continuing the oral immunotherapy if not carefully addressed, as the patient may lose tolerance to the peanut protein. To limit adverse events, the patient should continue the oral immunotherapy following one or more consecutive missed doses according to the guidance provided herein.

A patient undergoing peanut OIT for treatment of a peanut allergy generally has a known or suspected peanut allergy. Methods of diagnosing peanut allergy are known in the art and include a clinical history of allergic reaction following peanut ingestion, immunological assays (such as measuring peanut-specific IgE (ps-IgE) levels), skin prick tests, and food challenges. For diagnosis of peanut allergy by food challenge, the patient generally receives increasing doses of peanut protein, and an observed allergic reaction to the peanut protein during the food challenge indicates the patient has a peanut allergy.

A patient undergoing peanut OIT for treatment of a peanut allergy may be treatment naïve, having never undergone a peanut OIT for the treatment of a peanut allergy, or may have previously been treated for a peanut allergy either by oral immunotherapy or by another treatment method. A patient being diagnosed for peanut allergy by diagnostic exposure to peanut protein, such as in a food challenge, but with no other history of clinical exposure to peanut protein, is still considered treatment naïve after the diagnostic exposure for the purposes of this application.

The patient receiving the oral immunotherapy treatment for peanut allergy is a human patient. In some embodiments, the patient is about 1 year of age or older, such as between 1 year of age and about 4 years of age, about 4 years of age and about 12 years of age, between about 12 years of age and about 18 years of age, between about 18 years of age and about 26 years of age, or about 26 years of age or older.

FIG. 1 shows an exemplary oral immunotherapy dosing schedule. The illustrated oral immunotherapy begins with the optional initial escalation phase, which includes oral administration of a series of escalating doses ranging from about 0.5 mg to about 6 mg of peanut protein, which are administered in the same day and spaced by about 20 to about 30 minutes. During this phase, the patient can be monitored for an adverse event under medical supervision, and a medical caregiver can assess the suitability of the oral immunotherapy treatment for the patient. Upon completion of the optional initial escalation phase, the patient begins the up-dosing phase of the treatment. During the up-dosing phase, the subject receives daily scheduled doses of the pharmaceutical composition comprising peanut protein. The same dose is administered on a daily basis for a period of time, before the dose is increased. According to the schedule illustrated in FIG. 1, the patient receives the same dose for two weeks before the dose is escalated. However, that two week period may be longer (for example about 2 weeks to about 4 weeks), or may be shorter (for example, about 1 week to about 2 weeks). The scheduled period of time may be predetermined, or may be adjusted based on the reaction of the patient to the pharmaceutical composition. For example, if the patient experiences no allergic adverse events or only mild allergic adverse events, the period of time may be two weeks before the dose is escalated. On the other hand, if the patient experiences a moderate or severe allergic adverse event, the oral immunotherapy dosing schedule may be adjusted such that the dose escalation is delayed or the dose may be reduced. In addition to allergenic adverse events, the dosing schedule may be adjusted for other concurring factors, such as an infection, inflammation (for example due to surgery, a traumatic injury), menses, or other concurring factors that may lead to heightened sensitivity to the peanut protein. In the example illustrated in FIG. 1, the up-dosing phase includes doses of about 3 mg, about 6 mg, about 12 mg, about 20 mg, about 40 mg, about 80 mg, about 120 mg, about 160 mg, about 200 mg, about 240 mg, and about 300 mg peanut protein, which are administered to the patient in an escalating manner. However, other suitable doses may be used during the up-dosing phase, and (as discussed above), the scheduled dose may be reduced based on the status of the patient. Following the up-dosing phase in the scheduled oral immunotherapy is a maintenance phase, which includes the regular oral administration of a maintenance dose. In some embodiments, the maintenance dose is administered on a daily basis. The maintenance dose may be the same dose as the highest dose reached during the up-dosing phase, but, in some embodiments, it may be higher or lower than the highest dose level. The maintenance phase is administered to the patient to maintain the state of desensitization.

To administer the pharmaceutical composition comprising the peanut protein, the composition is orally ingested. Although the pharmaceutical composition may be packaged in an edible dosage form (e.g., a capsule), the pharmaceutical composition is usually removed from the package to allow sufficient oral contact. For example, the pharmaceutical composition may be mixed with a food vehicle, such as oatmeal, pudding, applesauce, yogurt, or other semi-solid food and eaten.

Up-Dosing Phase

The up-dosing phase includes orally administering to the patient a series of escalating doses of the pharmaceutical composition on a daily basis, wherein a given dose is administered to the patient for at least a predetermined period of time before the dose is escalated to reach the maximum dose administered to the patient during the course of the oral immunotherapy. The length of time of the up-dosing phase can be adapted according to the needs of an individual patient, although is generally completed in about 22 to about 40 weeks. For some patients, the up-dosing phase may last as long as 2 years or more. The up-dosing phase may be extended, for example, if a patient experiences allergic adverse events after beginning a higher dose in the dosing series.

The pharmaceutical composition administered to the patient during the up-dosing phase is administered at pre-set escalating dose levels. The patient slowly escalates the dose levels under medical direction until a maximum dose is reached, generally the same dose as the maintenance dose. The same dose level (i.e., the same dose of peanut protein) is administered to the patient for a period of time as the patient becomes desensitized to that amount before the dose level is increased. In some embodiments, the up-dosing phase comprises a series of escalating doses of the pharmaceutical composition at about 5 or more different dose levels (for example 5 to 15 different dose levels, such as 5, 6, 7, 8, 9, 10, 11, 12, 13, 14, or 15 different dose levels). In a non-limiting preferred embodiment, the up-dosing phase includes 11 different dose levels. For example, the up-dosing phase may include dose levels of about 3 mg, about 6 mg, about 12 mg, about 20 mg, about 40 mg, about 80 mg, about 120 mg, about 160 mg, about 200 mg, about 240 mg, and about 300 mg peanut protein.

The up-dosing phase of a peanut OIT typically involves incrementally increasing the administered peanut protein dose after a period of time (e.g., approximately every 1-4 weeks). A particular dose in the series is repeatedly (e.g., daily) administered to the patient until advancing to the next dose in the series. In some instances, such as when the patient does not tolerate a particular dose in the series or the patient experiences one or more allergic adverse events, the dose is decreased or the dose in the series is repeated for a period of time prior to advancing to the next dose in the series. The rate of up-dosing (e.g., the length of time an individual dose in the series is administered or the size of the dose increment between doses in the series) may be adjusted based on one or more observed allergic adverse events.

The doses administered to the patient during the up-dosing phase are generally administered on a daily basis for a period of time, such as about 1 week to about 4 weeks, such as about 2 weeks. After the completion of a particular dose in the series for a period of time, treatment can be advanced to a higher dose in the series. In some embodiments, the up-dosing phase of the treatment comprises a series of between 5 and 15 different dose levels. If a patient tolerates a particular dose level during the up-dosing phase for a period of time, the patient can advance to the next dose level in the series of the up-dosing phase. If a patient does not tolerate a particular dose level during the up-dosing phase for a period of time, the patient may repeat the current dose level in the series. Alternatively, if a patient does not tolerate a particular dose level during the up-dosing phase for a period of time, the patient may return to an earlier dose level in the series. The duration of the up-dosing phase therefore depends on the specific responses of the patient. The patient may repeat doses in the series as many times as necessary to achieve the highest dose in the series. The up-dosing phase ends when the highest dose is tolerated for two weeks.

The dose levels of the pharmaceutical composition administered during the up-dosing phase are generally between about 0.5 mg and about 1000 mg of peanut protein, such as about 0.5 mg to about 10 mg peanut protein, about 10 mg to about 100 mg peanut protein, about 100 mg to about 300 mg peanut protein, about 300 mg to about 500 mg peanut protein, or about 500 mg to about 1000 mg peanut protein. In a non-limiting exemplary embodiment, the dose levels of the up-dosing phase include doses of about 3 mg peanut protein, about 6 mg peanut protein, about 12 mg peanut protein, about 20 mg peanut protein, about 40 mg peanut protein, about 80 mg peanut protein, about 120 mg peanut protein, about 160 mg peanut protein, about 200 mg peanut protein, about 240 mg peanut protein, and about 300 mg peanut protein, wherein each dose level is administered on a daily basis for about 1 week to about 4 weeks (such as about 2 weeks) before escalating to the next highest dose.

The doses administered to the patient during the up-dosing phase are adjusted periodically, such as between once every week and once every six weeks. In some embodiments, the up-dosing phase comprises weekly dose adjustment, dose adjustment every two weeks, dose adjustment every third week, dose adjust every fourth week, dose adjustment every fifth week, dose adjustment every sixth week, or adjustment as needed based on the judgment of the patient's medical caregiver. The dose may be increased to the next scheduled dose in the series, lowered to a previous in the series in response to an allergic adverse event, maintained for an additional period of time at the current dose in the series, increased to a higher dose in the series based on the judgment of the patient's medical caregiver, or decreased to a lower dose in the series based on the judgment of the patient's medical caregiver. In some embodiments, the up-dosing phase is adjusted at any time based on the judgment of the patient's medical caregiver that the patient did not tolerate the current dose in the series.

The up-dosing phase proceeds until the patient achieves the final dose in the up-dosing series. In some embodiments, the up-dosing phase is about 1 month to about 6 months, such as about 1 month to about 3 months, or about 3 months to about 6 months. In some embodiments, the up-dosing phase is about 6 months to about 2 years, such as about 6 months to about 1 year, about 1 year to about 18 months, or about 18 months to about 2 years. In a non-limiting exemplary embodiment, the up-dosing phase continues for 22 weeks to 2 years, depending on the number of dose reductions and re-escalations and dose level repeats, through doses of 12 mg peanut protein, 20 mg peanut protein, 40 mg peanut protein, 80 mg peanut protein, 120 mg peanut protein, 160 mg peanut protein, 200 mg peanut protein, 240 mg peanut protein, and terminating after a 300 mg peanut protein dose level. In another non-limiting exemplary embodiment, the up-dosing phase continues for 22 weeks to 2 years, depending on the number of dose reductions and re-escalations and dose level repeats, through doses of 3 mg peanut protein, 6 mg peanut protein, 12 mg peanut protein, 20 mg peanut protein, 40 mg peanut protein, 80 mg peanut protein, 120 mg peanut protein, 160 mg peanut protein, 200 mg peanut protein, 240 mg peanut protein, and terminating after a 300 mg peanut protein dose level. In any of the described embodiments, the up-dosing phase terminates when the patient tolerates the scheduled dose of the final dose in the series of the up-dosing phase for 2 weeks, thereby beginning the maintenance phase.

Each dose of the series of the up-dosing phase may be scheduled to last about 1 week, about 2 weeks, about 3 weeks, about 4 weeks, or values and ranges therebetween.

Based on the observation of an allergic adverse event, a patient's caregiver may repeat the patient's current dose in up-dosing series. A particular portion with a particular dose may be repeated as many times as necessary, such as once, two times, three times, or four times, or more, to adequately desensitize a patient to that dose, such as when the patient no longer experiences a moderate or serious allergic adverse event upon accidental (or deliberate) exposure to the food allergen.

Maintenance Phase

The maintenance phase of the oral immunotherapy begins after the termination of the up-dosing phase. In any of the methods described herein, the maintenance phase comprises orally administering to the patient a plurality of maintenance doses of the pharmaceutical composition.

The duration of the maintenance phase is generally about 20 weeks or longer, and may be for the entire life of the patient. For example, in some embodiments, the maintenance phase is about 20 weeks to about 24 weeks, about 24 weeks to about 28 weeks, about 28 weeks to about 32 weeks, about 32 weeks to about 36 weeks, about 36 weeks to about 40 weeks, about 40 weeks to about 44 weeks, about 44 weeks to about 48 weeks, about 48 weeks to about 52 weeks, about 52 weeks to about 60 weeks, about 60 weeks to about 72 weeks, about 72 weeks to about 80 weeks, or more than about 80 weeks, such as the life of the patient.

The dose of peanut protein administered to the patient during the maintenance phase is between about 200 mg and about 1000 mg peanut protein, unless the maintenance phase dose has been reduced for example according to the methods described herein when the patient misses one or more consecutive doses. For example, in some embodiments, a dose during the maintenance phase is between about 200 mg and about 300 mg peanut protein, about 300 mg and about 500 mg peanut protein, about 500 mg and about 1000 mg peanut protein, or values and ranges therebetween, unless the maintenance phase dose has been reduced for example according to the methods described herein when the patient misses one or more consecutive doses. The scheduled maintenance phase dose can be at the same dose or a higher dose as the dose administered during the final sub-phase of the up-dosing phase. In a non-limiting exemplary embodiment, a maintenance phase dose administered to the patient during the maintenance phase is about 300 mg peanut protein. In some embodiments, the maintenance phase dose is administered daily.

Initial Escalation Phase

Optionally, the oral immunotherapy includes an initial escalation phase before the up-dosing phase, wherein the patient is administered over the course of one or two days a series of escalating doses. The initial escalation phase is distinguished from the up-dosing phase by a lower dose range, shorter intervals between dose escalations, and, typically, closer monitoring by the patient's medical caregiver. For example, a two day initial escalation may comprise a series of doses from about 0.5 mg to about 6 mg peanut protein, such as individual doses of about 0.5 mg, about 1 mg, about 1.5 mg, about 3 mg, and about 6 mg peanut protein. The highest tolerated dose of the initial escalation phase, or a dose lower than the highest tolerated dose in the initial escalation phase, may be the first dose of the up-dosing phase. If a patient does not tolerate at least a certain dose in the initial escalation phase, the patient may be excluded from the oral immunotherapy as unsuitable for treatment at that time. For example, if a patient suffers a serious allergic adverse event after administration of the 0.5 mg, 1 mg, or 1.5 mg peanut protein dose, the patient may not be allowed to proceed to the up-dosing phase. The purposes of the initial escalation phase include calibrating the doses of the up-dosing phase (e.g., the initial dose of the up-dosing phase), and ensuring the suitability of the patient for safely entering an up-dosing phase.

The initial escalation phase is generally administered under medical supervision. The patient is usually closely monitored by a medical caregiver, who can provide interventions such as epinephrine, albuterol, and diphenhydramine in the event of an allergic adverse reaction that necessitates intervention. The initial escalation phase of the oral immunotherapy, if present, includes administration of a plurality of small doses of the peanut protein composition to the patient. The small doses can be spaced by a period of time, such as about 10 minutes to about 60 minutes, and can include 1, 2, 3, 4, or 5 or more doses.

In one example, the initial escalation phase comprises doses between about 0.5 mg and about 6 mg peanut protein, such as about 0.5 mg to about 1.5 mg peanut protein, about 1.5 mg to about 3 mg peanut protein, or about 3 mg to about 6 mg peanut protein. In a non-limiting example, the initial escalation phase comprises an incremental escalation over one day from about 0.5 mg peanut protein to a maximum of about 6 mg peanut protein in a single day, with single doses of about 0.5 mg, about 1 mg, about 1.5 mg, about 3 mg, and about 6 mg of peanut protein, wherein tolerance of the 3 mg or 6 mg peanut protein dose indicates the patient can safely proceed to an up-dosing phase of an oral immunotherapy.

Methods for Continuing Oral Immunotherapy After One or More Missed Consecutive Doses During an oral immunotherapy, a patient may occasionally miss one or more scheduled oral administrations of the pharmaceutical composition. The one or more scheduled doses may be missed during either the up-dosing phase or the maintenance phase of the oral immunotherapy. The dose may be unintentionally missed (for example, a patient or caregiver may have forgotten to administer the dose to the patient), or the dose may be intentionally missed (for example, a medical caregiver may order one or consecutive doses to be skipped in response to an adverse event experienced by the patient or other compounding factor experienced by the patient). Described herein are methods of continuing an oral immunotherapy for the treatment of a peanut allergy in a patient after missing a scheduled oral administration of one or more consecutive doses of a pharmaceutical composition comprising peanut protein, the oral immunotherapy comprising (i) an up-dosing phase comprising orally administering to the patient a series of escalating doses of the pharmaceutical composition on a daily basis, wherein a given dose is administered to the patient for at least a predetermined period of time before the dose is escalated, and (ii) a maintenance phase comprising orally administering to the patient a plurality of maintenance doses of the pharmaceutical composition, the method comprising orally administering to the patient a dose of the pharmaceutical composition after missing the scheduled one or more consecutive doses in accordance with the conditions described herein to ensure safe continuation of the oral immunotherapy.

Consecutively missed doses raise more of a concern for safely continuing the oral immunotherapy than a single isolated missed dose, as the there is a risk the tolerance built up during the up-dosing phase may be quickly diminished if there is no regular exposure to the peanut protein. As administration of the dose is scheduled according to the oral immunotherapy (for example, daily administration), two or more consecutive doses refers to doses that are temporally proximal to each other according to the schedule. For example, if a schedule requires dose administration on days 1, 2, 3, 4, 5, 6, and 7; and a dose was administered to the patient only on days 1, 2, 3, and 7; then the missed doses on days 4, 5, and 6 would constitute three consecutively missed doses. A single missed dose is considered to be "one consecutive dose" missed.

The size of the dose and the manner in which it is administered to the patient (i.e., whether the dose is administered under medical supervision or without medical supervision) is based, at least in part, on the number of missed consecutive doses. In some embodiments, an individualized objective assessment of the patient is made, and this assessment is used as a basis for the size and manner of dose administration. This decision may be made, for example, by the patient's medical caregiver. Nevertheless, the guidelines provided herein should be used with continuing the oral immunotherapy after one or more consecutive does scheduled to be administered have been missed. The oral immunotherapy schedule may comprise administration of the scheduled dose at a particular time of day, such as morning, afternoon, evening, night, after waking, or before sleeping. In some embodiments, the methods of continuing the oral immunotherapy comprise administered the next dose after the one or more consecutive doses are missed at the same time of day according to the oral immunotherapy schedule. In some embodiments, the guidelines may apply differently to a set number of consecutive doses missed during the up-dosing phase (e.g., stricter guidelines may be applied) compared to the guidelines applied to the same number of consecutive doses missed during the maintenance phase.

In some embodiments, between 1 and 21 consecutive doses are missed (for example, 1, 2, 3, 4, 5, 6, 7, 8, 9, 10, 11, 12, 13, 14, 15, 16, 17, 18, 19, 20, or 21 consecutive doses are missed). In some embodiments, the consecutive doses are missed during the up-dosing phase. In some embodiments, the consecutive doses are missed during the maintenance phase. The guidelines for the size and manner of the dose administered to the patient can differ depending on how many doses were missed, as increased precautions should be taken when more consecutive doses are missed. For example, a first guideline may apply if the patient misses 1 to 5 consecutive doses (or 1 to 4, 1 to 3, 1 to 2 consecutive doses, or 1 dose). A second guideline may apply if the patient misses 2 to 7 consecutive doses (or 2 to 6, 2 to 5, 2 to 4, 2 to 3, 3 to 7, 3 to 6, 3 to 5, 3 to 4, 4 to 7, 4 to 6, 4 to 5, 5 to 7, 5 to 6, 6 to 7 consecutive doses; or 2, 3, 4, 5, 6, or 7 consecutive doses). A third guideline may apply if the patient misses 3 to 21 consecutive doses (or 3 to any one of 20, 19, 18, 17, 16, 15, 14, 13, 12, 11, 10, 9, 8, 7, 6, 5, or 4 consecutive doses; 4 to any one of 21, 20, 19, 18, 17, 16, 15, 14, 13, 12, 11, 10, 9, 8, 7, 6, or 5 consecutive doses; 5 to any one of 21, 20, 19, 18, 17, 16, 15, 14, 13, 12, 11, 10, 9, 8, 7, or 6 consecutive doses; 6 to any one of 21, 20, 19, 18, 17, 16, 15, 14, 13, 12, 11, 10, 9, 8, or 7 consecutive doses; 7 to any one of 21, 20, 19, 18, 17, 16, 15, 14, 13, 12, 11, 10, 9, or 8 consecutive doses; 8 to any one of 21, 20, 19, 18, 17, 16, 15, 14, 13, 12, 11, 10, or 9 consecutive doses; 9 to any one of 21, 20, 19, 18, 17, 16, 15, 14, 13, 12, 11, or 10 consecutive doses; 10 to any one of 21, 20, 19, 18, 17, 16, 15, 14, 13, 12, or 11 consecutive doses; 11 to any one of 21, 20, 19, 18, 17, 16, 15, 14, 13, or 12 consecutive doses; 12 to any one of 21, 20, 19, 18, 17, 16, 15, 14, or 13 consecutive doses; 13 to any one of 21, 20, 19, 18, 17, 16, 15, or 14 consecutive doses; 14 to any one of 21, 20, 19, 18, 17, 16, or 15 consecutive doses; 15 to any one of 21, 20, 19, 18, 17, or 16 consecutive doses; 16 to any one of 21, 20, 19, 18, 17, or 16 consecutive doses; 17 to any one of 21, 20, 19, or 18 consecutive doses; 18 to 21, 18 to 20, or 18 to 19 consecutive doses; 19 to 21, or 19 to 20 consecutive doses; or 3, 4, 5, 6, 7, 8, 9, 10, 11, 12, 13, 14, 15, 16, 17, 18, 19, 20, or 21 consecutive doses). A fourth guideline may apply if the patient misses 4 or more consecutive doses (such as 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, or 22 or more consecutive doses). A method for continuing the dose administration after missing one or more missed doses preferably has non-overlapping guidances (that is, the number of missed doses for the first guidance, the second guidance, the third guidance, and the fourth guidance preferably relate to non-overlapping numbers of consecutive missed doses).

Missed doses present a safety risk and, further, may reduce the efficacy of the immunotherapy at any stage/phase of the immunotherapy. The one or more consecutive missed doses may be missed during any portion of the immunotherapy. In some embodiments, the one or more consecutive missed doses occur during the up-dosing phase. In some embodiments, the one or more consecutive missed doses occur during the maintenance phase.

The up-dosing phase is intended to induce desensitization, whereas the maintenance phase is intended to maintain the desensitized state. Patients missing doses during the up-dosing phase may more rapidly lose their achieved level of desensitization compared to the same number of missed doses during the maintenance phase. Consecutive doses missed during the up-dosing phase may therefore require stricter guidelines, such as a greater reduction in dose, compared to the same number of consecutive doses being missed during the maintenance phase. Therefore, the described guidelines may also differ depending upon whether the consecutive doses were missed during the up-dosing phase compared to the same number of consecutive doses being missed during the maintenance phase. For example, in an exemplary embodiment, a different guideline may be applied if a patient misses between 8 and 14 consecutive doses in the up-dosing phase compared to said patient missing the same number of consecutive doses during the maintenance phase.

If a patient misses consecutive doses during the up-dosing phase, and the guideline prescribes a dose reduction, the patient is administered a dose according to the up-dosing schedule that corresponds to the indicated dose reduction. The patient then repeats the up-dosing phase from that reduced dose level. For example, in an oral immunotherapy comprising up-dosing levels of 3 mg, 6 mg, 12 mg, 20 mg, 40 mg, 80 mg, 120 mg, 160 mg, 200 mg, 240 mg, and 300 mg of peanut protein for approximately 2 weeks per dose level, if a patient at a dose level of 240 mg misses a set number of consecutive doses indicating a dose reduction of 50% or more, then the next dose the patient receives would be 120 mg or less (i.e., a reduction of 50% or more). The patient would then continue the up-dosing phase as normal from the 120 mg dose level (or the dose level below 120 mg if a lower dose level is prescribed by the patient's medical provider); specifically, the patient would undergo approximately 2 weeks of dosing at each indicated dose level, such as 120 mg, 160 mg, 200 mg, 240 mg, and then 300 mg before transitioning to the maintenance phase, if each dose level is tolerated. In the event the dose administered after the missed consecutive doses is not tolerated, then a patient's medical provider would assess the patient and determine whether to repeat the dose level, reduce the dose level further, temporarily suspend the oral immunotherapy (e.g., a 1-week dose holiday), or discontinue the oral immunotherapy (e.g., if the patient has a history of non-compliance or adverse allergic reactions to oral immunotherapy). In some cases, a prescribed dose reduction may not be possible under the oral immunotherapy schedule. For example, given the preceding exemplary oral immunotherapy schedule, if a patient misses consecutive doses during the 3 mg dose level and the guidelines prescribe a dose reduction of 50% or more, or if the patient misses consecutive doses during the 6 mg dose level and the guidelines prescribe a dose reduction of 75% or more, then the prescribed dose reduction is not possible under the dose schedule. In such cases, for the purposes of this application, it is understood that the dose reduction means the patient should either restart the oral immunotherapy schedule (i.e., the patient is administered the initial dose of the up-dosing schedule) or discontinue the oral immunotherapy.

If a patient misses consecutive doses during the maintenance phase, and the guideline prescribes a dose reduction, the maintenance phase is understood to end and the patient is administered a dose according to the up-dosing schedule that corresponds to the indicated dose reduction (i.e., the patient returns to the up-dosing phase). For example, in an oral immunotherapy comprising up-dosing levels of 3 mg, 6 mg, 12 mg, 20 mg, 40 mg, 80 mg, 120 mg, 160 mg, 200 mg, 240 mg, and 300 mg of peanut protein for approximately 2 weeks per dose level and a maintenance phase comprising a dose level of 300 mg of peanut protein, if a patient receiving a 300 mg maintenance dose misses a set number of consecutive doses indicating a dose reduction of 50% or more, then the next dose the patient receives would be the up-dosing phase dose of 120 mg or less (i.e., a reduction of 50% or more). The patient would then continue the up-dosing phase as normal from the indicated dose level, such as the 120 mg dose level; specifically, the patient would undergo approximately 2 weeks of dosing at each of the indicated dose levels, such as 2 weeks each of 120 mg, 160 mg, 200 mg, 240 mg, and then 300 mg before transitioning back to the maintenance phase of 300 mg peanut protein, if each dose level is tolerated. In the event the dose administered after the missed consecutive doses is not tolerated, then a patient's medical provider would assess the patient and determine whether to repeat the dose level, reduce the dose level further, temporarily suspend the oral immunotherapy (e.g., a 1-week dose holiday), or discontinue the oral immunotherapy (e.g., if the patient has a history of non-compliance or adverse allergic reactions to oral immunotherapy). By restarting the up-dosing phase in this manner, any desensitization lost due to the missed consecutive doses during the maintenance phase can be rebuilt, without completely repeating the up-dosing phase. However, in some embodiments, if many consecutive doses are missed during the maintenance phase, the patient must either restart the up-dosing phase from the lowest dose (e.g., 3 mg peanut protein in the preceding example) or discontinue the oral immunotherapy. In an exemplary embodiment, if more than 14 consecutive doses (i.e., 15 or more doses) are missed during the maintenance phase, the patient restarts the up-dosing phase at the lowest up-dosing dose level.

If few consecutive doses are missed, the oral immunotherapy can be continued by administering a dose of the pharmaceutical composition after missing the scheduled doses, wherein the administered dose is the same as the most recently administered dose (i.e., the dose administered to the patient just before the missed dose(s)). The dose may be administered to the subject under medical supervision or without medical supervision. This guideline may apply if 1 to 5 consecutive doses are missed (or 1 to 4, 1 to 3, 1 to 2, 2 to 4, 2 to 3, or 3 to 4 consecutive doses are missed, or 1 dose is missed). In some embodiments, this guideline applies if one or two consecutive doses are missed.

As additional consecutive doses are missed, the risk to the patient of an allergenic adverse event is increased. To address this, the dose administered to the patient after several missed consecutive doses may be reduced and/or administered under medical supervision. For example, a dose administered to the patient after missing a set number of consecutive doses (e.g., 2 to 7, 2 to 6, 2 to 5, 2 to 4, 2 to 3, 3 to 7, 3 to 6, 3 to 5, 3 to 4, 4 to 7, 4 to 6, 4 to 5, 5 to 7, 5 to 6, 6 to 7 consecutive doses; or 2, 3, 4, 5, 6, or 7 consecutive doses) may be (i) the same as the dose most recently administered to the patient, but the dose is administered under medical supervision, or (ii) the dose is reduced compared to the most recently administered dose (for example by about 10% or more, about 15% or more, about 20% or more, about 25% or more, about 30% or more, about 35% or more, about 40% or more, about 50% or more, or by about 1, 2, 3, 4 or 5 dose levels), and can be administered under medical supervision or without medical supervision. The patient's medical caregiver can assess the patient to determine the size or manner in which the dose is administered to the patient, and may depend on the reason for the one or more consecutive missed doses, patient history, or status of the patient. The assessment to determine the size or manner in which the dose is administered to the patient may also depend on whether the missed consecutive doses were missed during the up-dosing phase or the maintenance phase.

A dose administered under medical supervision may be administered at a clinic by a medical caregiver/professional who is monitoring the patient for a treatment-related adverse event. The patient may be monitored for a treatment-related adverse event for a period of time (e.g., about 30 to about 60 minutes) after administration of the dose is administered, or until treatment-related adverse events resolve.

A patient's medical caregiver may advise the patient whether a dose after the one or more consecutive missed doses should be administered without medical supervision or under medical supervision, or whether the dose administered to the patient should be reduced. The decision to administer a dose after the one or more consecutive missed doses under medical supervision may depend, in part, on the history of adverse events of the patient. In some embodiments, a dose after the one or more consecutive missed doses is administered under medical supervision if the patient has any record during the immunotherapy of treatment-related adverse events of any grade. In some embodiments, a dose after the one or more consecutive missed doses is administered under medical supervision if the patient has any record during the immunotherapy of moderate or serious treatment-related adverse events. A dose after the one or more consecutive missed doses may be administered under medical supervision if the patient is assessed as otherwise at risk of treatment-related adverse events. In some embodiments, the patient is assessed as otherwise at risk of a treatment-related adverse event due to complicating factors (also sometimes known as compounding factors or risk factors) such as: if the patient has a comorbid atopic disease (such as asthma, dermatitis, or rhinitis). In some embodiments, the patient is assessed as otherwise at risk of a treatment-related adverse event based on immunological serum profile, including total IgE level, peanut-specific IgE level, and/or peanut-specific IgG4 level.

A patient may miss so many consecutive doses a reduction of the dose administered to the patient after the missed doses is suggested, whether or not the dose is administered under medical supervision. In some embodiments, this guideline applies if the administration of 3 to any one of 21, 20, 19, 18, 17, 16, 15, 14, 13, 12, 11, 10, 9, 8, 7, 6, 5, or 4 consecutive doses are missed; 4 to any one of 21, 20, 19, 18, 17, 16, 15, 14, 13, 12, 11, 10, 9, 8, 7, 6, or 5 consecutive doses are missed; 5 to any one of 21, 20, 19, 18, 17, 16, 15, 14, 13, 12, 11, 10, 9, 8, 7, or 6 consecutive doses are missed; 6 to any one of 21, 20, 19, 18, 17, 16, 15, 14, 13, 12, 11, 10, 9, 8, or 7 consecutive doses are missed; 7 to any one of 21, 20, 19, 18, 17, 16, 15, 14, 13, 12, 11, 10, 9, or 8 consecutive doses are missed; 8 to any one of 21, 20, 19, 18, 17, 16, 15, 14, 13, 12, 11, 10, or 9 consecutive doses are missed; 9 to any one of 21, 20, 19, 18, 17, 16, 15, 14, 13, 12, 11, or 10 consecutive doses are missed; 10 to any one of 21, 20, 19, 18, 17, 16, 15, 14, 13, 12, or 11 consecutive doses are missed; 11 to any one of 21, 20, 19, 18, 17, 16, 15, 14, 13, or 12 consecutive dose are missed; 12 to any one of 21, 20, 19, 18, 17, 16, 15, 14, or 13 consecutive doses are missed; 13 to any one of 21, 20, 19, 18, 17, 16, 15, or 14 consecutive doses are missed; 14 to any one of 21, 20, 19, 18, 17, 16, or 15 consecutive doses are missed; 15 to any one of 21, 20, 19, 18, 17, or 16 consecutive doses are missed; 16 to any one of 21, 20, 19, 18, 17, or 16 consecutive doses are missed; 17 to any one of 21, 20, 19, or 18 consecutive doses are missed; 18 to 21, 18 to 20, or 18 to 19 consecutive doses are missed; 19 to 21, or 19 to 20 consecutive doses are missed; or 3, 4, 5, 6, 7, 8, 9, 10, 11, 12, 13, 14, 15, 16, 17, 18, 19, 20, or 21 consecutive doses are missed. The dose reduction compared to the most recently administered dose may be about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, or about 95% or more as compared to the most recently administered dose of the up-dosing phase or maintenance phase. In some embodiments, the dose may be reduced by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% compared to the most recently administered dose, wherein the reduced amount is rounded down to the nearest dose that is part of the oral immunotherapy schedule. In a non-limiting exemplary embodiment, the dose to be administered after the one or more consecutive missed doses is reduced to a dose of about 3 mg peanut protein, about 6 mg peanut protein, about 12 mg peanut protein, about 20 mg peanut protein, about 40 mg peanut protein, about 80 mg peanut protein, about 120 mg peanut protein, about 160 mg peanut protein, about 200 mg peanut protein, or about 240 mg peanut protein.

If a relatively large number of consecutive doses are missed, whether during the up-dosing phase or the maintenance phase, it may be suggested that the patient re-start the up-dosing phase of the oral immunotherapy, starting at the initial dose (i.e., the first dose level) of the up-dosing phase. This guidance may apply if the administration of about 4 or more consecutive doses (such as 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, or 22 or more consecutive doses) are missed. In some embodiments, the initial dose of the up-dosing phase is about 0.5 mg to about 6 mg peanut protein (such as about 0.5 mg, about 1 mg, about 1.5 mg, about 3 mg, or about 6 mg peanut protein). In some embodiments, restarting the up-dosing phase of the oral immunotherapy does not include repeating the initial escalation phase of the oral immunotherapy.

An exemplary method for continuing an oral immunotherapy for the treatment of a peanut allergy in a patient after missing a scheduled administration of one or more consecutive doses of a pharmaceutical composition comprising peanut protein comprises orally administering to the patient a dose of the pharmaceutical composition after missing the scheduled one or more consecutive doses can include the following conditions: (1) if one to x consecutive doses are missed, the dose administered to the patient is the same as the most recently administered dose; (2) if (x+1) to y consecutive doses are missed, (i) the dose administered to the patient is the same as the most recently administered dose and the dose is administered to the patient under medical supervision, or (ii) the dose administered to the patient is reduced compared to the most recently administered dose; (3) if (y+1) to z consecutive doses are missed, the dose administered to the patient is reduced by about 25% or more (or about 50% or more); and (4) if more than z consecutive doses are missed, the dose administered to the patient is an initial dose of the up-dosing phase; wherein x, y, and z are positive integers, and x<y<z. In some embodiments, x is 1, 2, 3, 4, or 5 consecutive missed doses. In some embodiments, y is 2, 3, 4, 5, 6, or 7 consecutive missed doses, such as 3, 4, 5, 6, or 7 consecutive missed doses. In some embodiments, z is 3, 4, 5, 6, 7, 8, 9, 10, 11, 12, 13, 14, 15, 16, 17, 18, 19, 20, or 21 consecutive missed doses. In some embodiments, z is fourteen or more consecutive missed doses. In an exemplary embodiment, x is two, y is four, and z is fourteen. In another exemplary embodiment, x is two, y is seven, and z is fourteen. In some embodiments, the consecutive missed doses are during the up-dosing phase. In some embodiments, the consecutive missed doses are during the maintenance phase. In some embodiments, if a dose reduction is indicated, the dose reduction is increased (i.e., the administered dose is reduced) if the consecutive missed doses are missed during the up-dosing phase compared to the same number of doses being missed in the maintenance phase. In some embodiments, a dose reduction is indicated if the consecutive missed doses are missed during the up-dosing phase, and a dose reduction is not indicated if the same number of consecutive missed doses are missed during the maintenance phase.

In another exemplary method for continuing an oral immunotherapy for the treatment of a peanut allergy in a patient after missing a scheduled administration, during the up-dosing phase, of one or more consecutive doses of a pharmaceutical composition comprising peanut protein comprises orally administering to the patient a dose of the pharmaceutical composition after missing the scheduled one or more consecutive doses can include the following conditions: (1) if one to x consecutive doses are missed, the dose administered to the patient is the same as the most recently administered dose; (2) if (x+1) to y consecutive doses are missed, (i) the dose administered to the patient is the same as the most recently administered dose and the dose is administered to the patient under medical supervision, or (ii) the dose administered to the patient is reduced by about 50% or more compared to the most recently administered dose; (3) if (y+1) to z consecutive doses are missed, the dose administered to the patient is reduced by about 75% or more compared to the most recently administered dose; and (4) if more than z consecutive doses are missed, the dose administered to the patient is an initial dose of the up-dosing phase; wherein x, y, and z are positive integers, and x<y<z. In some embodiments, x is 1, 2, 3, 4, or 5 consecutive missed doses. In some embodiments, y is 2, 3, 4, 5, 6, or 7 consecutive missed doses, such as 3, 4, 5, 6, or 7 consecutive missed doses. In some embodiments, z is 3, 4, 5, 6, 7, 8, 9, 10, 11, 12, 13, 14, 15, 16, 17, 18, 19, 20, or 21 consecutive missed doses. In some embodiments, z is fourteen or more consecutive missed doses. In an exemplary embodiment, x is two, y is seven, and z is fourteen.

In another exemplary method for continuing an oral immunotherapy for the treatment of a peanut allergy in a patient after missing a scheduled administration, during the maintenance phase, of one or more consecutive doses of a pharmaceutical composition comprising peanut protein comprises orally administering to the patient a dose of the pharmaceutical composition after missing the scheduled one or more consecutive doses can include the following conditions: (1) if one to x consecutive doses are missed, the dose administered to the patient is the same as the most recently administered dose; (2) if (x+1) to y consecutive doses are missed, (i) the dose administered to the patient is the same as the most recently administered dose and the dose is administered to the patient under medical supervision, or (ii) the dose administered to the patient is reduced by about 50% or more compared to the most recently administered dose; (3) if (y+1) to z consecutive doses are missed, the dose administered to the patient is reduced by about 50% or more compared to the most recently administered dose; and (4) if more than z consecutive doses are missed, the dose administered to the patient is an initial dose of the up-dosing phase; wherein x, y, and z are positive integers, and x<y<z. In some embodiments, x is 1, 2, 3, 4, or 5 consecutive missed doses. In some embodiments, y is 2, 3, 4, 5, 6, or 7 consecutive missed doses, such as 3, 4, 5, 6, or 7 consecutive missed doses. In some embodiments, z is 3, 4, 5, 6, 7, 8, 9, 10, 11, 12, 13, 14, 15, 16, 17, 18, 19, 20, or 21 consecutive missed doses. In some embodiments, z is fourteen or more consecutive missed doses. In an exemplary embodiment, x is two, y is seven, and z is fourteen.

In one example, a method of continuing an oral immunotherapy for the treatment of a peanut allergy in a patient after missing a scheduled administration of one or more consecutive doses of a pharmaceutical composition comprising peanut protein comprises orally administering to the patient, without medical supervision, a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed, (i) the dose administered to the patient is the same as the most recently administered dose and the dose is administered to the patient under medical supervision, or (ii) the dose administered to the patient is reduced compared to the most recently administered dose; (3) if five to fourteen consecutive doses are missed, the dose administered to the patient is reduced by about 50% or more; and (4) if more than fourteen consecutive doses are missed, the dose administered to the patient is an initial dose of an up-dosing phase.

In another example, a method of continuing an oral immunotherapy for the treatment of a peanut allergy in a patient after missing a scheduled administration of one or more consecutive doses of a pharmaceutical composition comprising peanut protein comprises orally administering to the patient a dose of the pharmaceutical composition after missing the scheduled one or more consecutive doses, wherein: (1) if one or two consecutive doses are missed, the dose administered to the patient is the same as the most recently administered dose and the dose is administered without medical supervision; (2) if three or four consecutive doses are missed, the dose administered to the patient is the same as the most recently administered dose and the dose is administered to the patient under medical supervision; (3) if five to fourteen consecutive doses are missed, the dose administered to the patient is reduced by about 50% or more, and the dose is administered under medical supervision; and (4) if more than fourteen consecutive doses are missed, the dose administered to the patient is an initial dose of an up-dosing phase, and the dose is administered under medical supervision.

In another example, a method of continuing an oral immunotherapy for the treatment of a peanut allergy in a patient after missing a scheduled administration of one or more consecutive doses of a pharmaceutical composition comprising peanut protein comprises orally administering to the patient a dose of the pharmaceutical composition after missing the scheduled one or more consecutive doses, wherein: (1) if one or two consecutive doses are missed, the dose administered to the patient is the same as the most recently administered dose and the dose is administered without medical supervision; (2) if three or four consecutive doses are missed, the dose administered to the patient is the same as the most recently administered dose and the dose is administered to the patient under medical supervision; (3) if five to seven consecutive doses are missed, the dose administered to the patient is reduced by about 50% or more, and the dose is administered under medical supervision; (4) if eight to fourteen consecutive doses are missed, (i) the dose administered to the patient is reduced by about 50% or more, and the dose is administered under medical supervision, or (ii) the dose administered to the patient is reduced by about 75% or more, and the dose is administered to the patient under medical supervision; and (5) if more than fourteen consecutive doses are missed, the dose administered to the patient is an initial dose of an up-dosing phase, and the dose is administered under medical supervision.

In another example, a method of continuing an oral immunotherapy for the treatment of a peanut allergy in a patient after missing a scheduled administration, during the up-dosing phase, of one or more consecutive doses of a pharmaceutical composition comprising peanut protein comprises orally administering to the patient a dose of the pharmaceutical composition after missing the scheduled one or more consecutive doses, wherein: (1) if one to two consecutive doses are missed, the dose administered to the patient is the same as the most recently administered dose and the dose is administered without medical supervision; (2) if three or four consecutive doses are missed, the dose administered to the patient is the same as the most recently administered dose and the dose is administered under medical supervision; (3) if five to seven consecutive doses are missed, the dose administered to the patient is reduced by about 50% or more compared to the most recently administered dose; (4) if eight to fourteen consecutive doses are missed, the dose administered to the patient is reduced by about 75% or more compared to the most recently administered dose; and (5) if more than fourteen consecutive doses are missed, the dose administered to the patient is an initial dose of an up-dosing phase.

In another example, a method of continuing an oral immunotherapy for the treatment of a peanut allergy in a patient after missing a scheduled administration, during the maintenance phase, of one or more consecutive doses of a pharmaceutical composition comprising peanut protein comprises orally administering to the patient a dose of the pharmaceutical composition after missing the scheduled one or more consecutive doses, wherein: (1) if one to two consecutive doses are missed, the dose administered to the patient is the same as the most recently administered dose and the dose is administered without medical supervision; (2) if three to four consecutive doses are missed, the dose administered to the patient is the same as the most recently administered dose and the dose is administered under medical supervision; (3) if five to seven consecutive doses are missed, the dose administered to the patient is reduced by about 50% or more compared to the most recently administered dose; (4) if eight to fourteen consecutive doses are missed, the dose administered to the patient is reduced by about 50% or more compared to the most recently administered dose; and (5) if more than fourteen consecutive doses are missed, the dose administered to the patient is an initial dose of an up-dosing phase.

In another example, a method of continuing an oral immunotherapy for the treatment of a peanut allergy in a patient after missing a scheduled administration of one or more consecutive doses of a pharmaceutical composition comprising peanut protein comprises orally administering to the patient, under medical supervision, a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed, (i) the dose administered to the patient is the same as the most recently administered dose and the dose is administered to the patient under medical supervision, or (ii) the dose administered to the patient is reduced compared to the most recently administered dose; (3) if five to fourteen consecutive doses are missed, the dose administered to the patient is reduced by about 50% or more; and (4) if more than fourteen consecutive doses are missed, the dose administered to the patient is an initial dose of an up-dosing phase.

In another example, a method of continuing an oral immunotherapy for the treatment of a peanut allergy in a patient after missing a scheduled administration of one or more consecutive doses of a pharmaceutical composition comprising peanut protein comprises orally administering to the patient, without medical supervision, a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed, (i) the dose administered to the patient is the same as the most recently administered dose and the dose is administered to the patient under medical supervision, or (ii) the dose administered to the patient is reduced compared to the most recently administered dose; and (3) if five to fourteen consecutive doses are missed, the dose administered to the patient is reduced by about 50% or more.

In another example, a method of continuing an oral immunotherapy for the treatment of a peanut allergy in a patient after missing a scheduled administration of one or more consecutive doses of a pharmaceutical composition comprising peanut protein comprises orally administering to the patient, under medical supervision, a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed, (i) the dose administered to the patient is the same as the most recently administered dose and the dose is administered to the patient under medical supervision, or (ii) the dose administered to the patient is reduced compared to the most recently administered dose; and (3) if five to fourteen consecutive doses are missed, the dose administered to the patient is reduced by about 50% or more.

In an exemplary embodiment, one or two consecutive doses were missed, the dose administered to the subject is the same as the most recently administered dose, and the dose is administered without medical supervision.

In an exemplary embodiment, one or two consecutive doses were missed, the dose administered to the subject is the same as the most recently administered dose, and the dose is administered under medical supervision.

In an exemplary embodiment, three or four consecutive doses were missed, the dose administered to the subject is the same dose as the most recently administered dose, and the dose is administered without medical supervision.

In an exemplary embodiment, three or four consecutive doses were missed, the dose administered to the subject is the same dose as the most recently administered dose, and the dose is administered under medical supervision.

In an exemplary embodiment, three or four consecutive doses were missed, the dose administered to the subject is reduced compared to the most recently administered dose, and the dose is administered without medical supervision.

In an exemplary embodiment, three or four consecutive doses were missed, the dose administered to the subject is reduced compared to the most recently administered dose, and the dose is administered under medical supervision.

In an exemplary embodiment, three or four consecutive doses were missed, the dose administered to the subject is reduced by 25% or more compared to the most recently administered dose, and the dose is administered without medical supervision.

In an exemplary embodiment, three or four consecutive doses were missed, the dose administered to the subject is reduced by 25% or more compared to the most recently administered dose, and the dose is administered under medical supervision.

In an exemplary embodiment, three or four consecutive doses were missed, the dose administered to the subject is reduced by 50% or more compared to the most recently administered dose, and the dose is administered without medical supervision.

In an exemplary embodiment, three or four consecutive doses were missed, the dose administered to the subject is reduced by 50% or more compared to the most recently administered dose, and the dose is administered under medical supervision.

In an exemplary embodiment, five to seven consecutive doses were missed, the dose administered to the subject is reduced by 25% or more compared to the most recently administered dose, and the dose is administered under medical supervision.

In an exemplary embodiment, five to seven consecutive doses were missed, the dose administered to the subject is reduced by 25% or more compared to the most recently administered dose, and the dose is administered without medical supervision.

In an exemplary embodiment, five to seven consecutive doses were missed, the dose administered to the subject is reduced by 50% or more compared to the most recently administered dose, and the dose is administered under medical supervision.

In an exemplary embodiment, five to seven consecutive doses were missed, the dose administered to the subject is reduced by 50% or more compared to the most recently administered dose, and the dose is administered without medical supervision.

In an exemplary embodiment, eight to fourteen consecutive doses were missed during the up-dosing phase, the dose administered to the subject is reduced by 50% or more compared to the most recently administered dose.

In an exemplary embodiment, eight to fourteen consecutive doses were missed during the up-dosing phase, the dose administered to the subject is reduced by 75% or more compared to the most recently administered dose.

In an exemplary embodiment, eight to fourteen consecutive doses were missed during the maintenance phase, the dose administered to the subject is reduced by 25% or more compared to the most recently administered dose.

In an exemplary embodiment, eight to fourteen consecutive doses were missed during the maintenance phase, the dose administered to the subject is reduced by 50% or more compared to the most recently administered dose.

In an exemplary embodiment, five to fourteen consecutive doses were missed, the dose administered to the subject is reduced by 50% or more compared to the most recently administered dose, and the dose is administered without medical supervision.

In an exemplary embodiment, five to fourteen consecutive doses were missed, the dose administered to the subject is reduced by 50% or more compared to the most recently administered dose, and the dose is administered under medical supervision.

In an exemplary embodiment, more than fourteen consecutive doses were missed, and the dose administered to the subject is an initial dose of the up-dosing phase.

In an exemplary embodiment, the up-dosing phase comprises a series of doses of a pharmaceutical composition comprising peanut protein comprising dose levels of 3 mg, 6 mg, 12 mg, 20 mg, 40 mg, 80 mg, 120 mg, 160 mg, 200 mg, 240 mg, 300 mg, and the maintenance phase comprises a dose level of 300 mg, and the method of continuing an oral immunotherapy for the treatment of peanut allergy in a patient after missing a scheduled administration of one or more consecutive doses of a pharmaceutical composition comprising peanut protein comprises orally administering to the patient a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed the dose administered to the patient is the same as the most recently administered dose and the dose is administered to the patient under medical supervision; (3) if five to seven consecutive doses are missed the dose administered to the patient is reduced by about 50% or more compared to the most recently administered dose; (4) if eight to fourteen consecutive doses are missed, the dose administered to the patient is (i) reduced by about 75% or more compared to the most recently administered dose if the doses were missed during the up-dosing phase, and (ii) reduced by about 50% or more compared to the most recently administered dose if the doses were missed during the maintenance phase; and (5) if more than fourteen consecutive doses are missed, the dose administered to the patient is the dose of the initial dose level of the up-dosing phase.

In an exemplary embodiment, the up-dosing phase comprises a series of doses of a pharmaceutical composition comprising peanut protein comprising dose levels of 3 mg, 6 mg, 12 mg, 20 mg, 40 mg, 80 mg, 120 mg, 160 mg, 200 mg, 240 mg, 300 mg, and the maintenance phase comprises a dose level of 300 mg, and the method of continuing an oral immunotherapy for the treatment of peanut allergy in a patient after missing a scheduled administration of one or more consecutive doses, during the up-dosing phase, of a pharmaceutical composition comprising peanut protein comprises orally administering to the patient a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed the dose administered to the patient is the same as the most recently administered dose and the dose is administered to the patient under medical supervision; (3) if five to seven consecutive doses are missed the dose administered to the patient is reduced by about 50% or more compared to the most recently administered dose; (4) if eight to fourteen consecutive doses are missed, the dose administered to the patient is reduced by about 75% or more compared to the most recently administered dose; and (5) if more than fourteen consecutive doses are missed, the dose administered to the patient is the dose of the initial dose level of the up-dosing phase.

In an exemplary embodiment, the up-dosing phase comprises a series of doses of a pharmaceutical composition comprising peanut protein comprising dose levels of 3 mg, 6 mg, 12 mg, 20 mg, 40 mg, 80 mg, 120 mg, 160 mg, 200 mg, 240 mg, 300 mg, and the maintenance phase comprises a dose level of 300 mg, and the method of continuing an oral immunotherapy for the treatment of peanut allergy in a patient after missing a scheduled administration of one or more consecutive doses, during the maintenance phase, of a pharmaceutical composition comprising peanut protein comprises orally administering to the patient a dose of the pharmaceutical composition after missing the scheduled one or more consecutive doses, wherein: (1) if one or two consecutive doses are missed, the dose administered to the patient is the same as the most recently administered dose; (2) if three or four consecutive doses are missed the dose administered to the patient is the same as the most recently administered dose and the dose is administered to the patient under medical supervision; (3) if five to seven consecutive doses are missed the dose administered to the patient is reduced by about 50% or more compared to the most recently administered dose; (4) if eight to fourteen consecutive doses are missed, the dose administered to the patient is reduced by about 50% or more compared to the most recently administered dose; and (5) if more than fourteen consecutive doses are missed, the dose administered to the patient is the dose of the initial dose level of the up-dosing phase.

FIG. 2 depicts an exemplary set of guidelines for consecutive missed doses that are missed during the up-dosing phase. If 1 to 2 consecutive missed doses are missed, the dosing is resumed at the same dose level without medical supervision. If 3 to 4 consecutive doses are missed, the dosing is resumed at the same dose level, but under medical supervision. If 5 to 7 consecutive doses are missed, the dosing is resumed under medical supervision at a dose reduction of 50% or more compared to the last administered dose. If 8 to 14 consecutive doses are missed, the dosing is resumed at a dose reduction of 75% or more compared to the last administered dose. If more than 14 consecutive doses are missed, then the dosing is resumed at the lowest initial up-dosing dose.

FIG. 3 depicts an exemplary set of guidelines for consecutive missed doses that are missed during the maintenance phase. If 1 to 2 consecutive doses are missed, the dosing is resumed at the same dose level without medical supervision. If 3 to 4 consecutive doses are missed, the dosing is resumed at the same level, but under medical supervision. If 5 to 7 consecutive doses are missed, the maintenance phase ends and the patient resumes up-dosing under medical supervision at a dose reduction of 50% or more compared to the last administered dose. If 8 to 14 doses are missed, the maintenance phase ends and the patient resumes up-doing under medical supervision at a dose reduction of 50% or more compared to the last administered dose. If greater than 14 consecutive doses are missed, the maintenance phase ends and the patient re-starts the up-dosing phase at the lowest initial up-dosing dose.

Compositions for Oral Immunotherapy

Exemplary compositions for treating peanut allergy are described in detail in U.S. Patent No. 2014/0271721. Exemplary methods for preparing peanut protein formulations are described in detail in U.S. Publication No. 2014/0271836.

A patient having a peanut allergy can be treated for the peanut allergy by administering a series of doses of a peanut protein composition to the patient during the course of a peanut protein oral immunotherapy. The peanut protein composition is preferably a pharmaceutical composition comprising one or more peanut allergen proteins for treating peanut allergy. In some embodiments, peanut proteins may be isolated from peanut flour and, optionally, further comprise one or more diluents, one or more glidants, and/or one or more lubricants. In some embodiments, the pharmaceutical composition of peanut protein comprises between about 0.05% to about 100% w/w of peanut protein.

In some embodiments, the pharmaceutical composition of peanut protein comprises characterized peanut protein. In some embodiments the characterized peanut protein comprises characterized peanut allergen proteins Ara h1, Ara h2, and/or Ara h6. In one embodiment, a final formulation for treating peanut allergy comprises peanut flour, comprising characterized peanut allergen proteins Ara h1, Ara h2, and/or Ara h6, formulated with a diluent, a glidant, and a lubricant in graduated doses comprising capsules containing between about 0.5 and about 5,000 mg of peanut protein for administration in up-dosing, maintenance, and/or initial escalation phases of an oral immunotherapy, including the dose after one or more consecutive missed doses, of an oral immunotherapy.

In any of the methods described herein, the pharmaceutical composition of peanut protein for administration in a maintenance phase of an oral immunotherapy may comprise a dose of between about 200 mg to about 1,000 mg peanut protein, such as between about 200 mg and about 250 mg peanut protein, about 250 mg and about 300 mg peanut protein, about 300 mg and about 500 mg peanut protein, and about 500 mg and about 1,000 mg peanut protein. In a non-limiting preferred embodiment, the dose of peanut protein for administration in the maintenance phase of an oral immunotherapy is about 300 mg peanut protein.

In some embodiments, the pharmaceutical composition of peanut protein for administration in an up-dosing phase of an oral immunotherapy comprises between about 0.5 mg and about 5,000 mg peanut protein, such as individual doses in a series of about 3 mg, about 6 mg, about 10 mg, about 12 mg, about 20 mg, about 40 mg, about 80 mg, about 100 mg, about 120 mg, about 160 mg, about 200 mg, about 240 mg, and about 300 mg peanut protein. In a non-limiting exemplary embodiment, the doses of peanut protein for administration in an up-dosing phase of an oral immunotherapy are daily administration of the maximum tolerated dose of the initial escalation phase, such as about 3 mg peanut protein or about 6 mg peanut protein, followed by a series of escalating daily doses prescribed by a patient's medical caregiver, wherein each daily dose comprises one or more capsules or sachets selected from the group consisting of: about 0.5 mg peanut protein capsules, about 1 mg peanut protein capsules, about 10 mg peanut protein capsules, about 20 mg peanut protein capsules, about 100 mg peanut protein capsules, or about 300 mg peanut protein sachets, wherein each dosage level is administered for about 1 week to about 4 weeks (such as about 2 weeks) before advancing to the next dose.

In any of the methods described herein, the pharmaceutical composition of peanut protein for administration to a patient as a dose after the one or more consecutive missed doses comprises between about 0.5 mg to about 1,000 mg peanut protein, such as about 1 mg to about 3 mg, about 3 mg to about 6 mg, about 6 mg to about 10 mg, about 10 mg to about 12 mg, about 12 mg to about 20 mg, about 20 mg to about 40 mg, about 40 mg to about 80 mg, about 80 mg to about 100 mg, about 100 mg to about 120 mg, about 120 mg to about 160 mg, about 160 mg to about 200 mg, about 200 mg to about 240 mg, about 240 mg to about 300 mg, about 300 mg to about 500 mg, and about 500 mg to about 1,000 mg peanut protein. In a non-limiting preferred embodiment, the dose of peanut protein for administration to a patient as a dose after the one or more consecutive missed doses is about 3 mg, about 6 mg, about 12 mg, about 20 mg, about 40 mg, about 80 mg, about 120 mg, about 160 mg, about 200 mg, about 240 mg, or about 300 mg peanut protein. In another non-limiting preferred embodiment, the dose of peanut protein for administration to a patient as a dose after the one or more consecutive missed doses is the first of a re-started up-dosing phase and is about 1 mg, about 3 mg, about 6 mg, about 12 mg, about 20 mg, about 40 mg, about 80 mg, or about 120 mg peanut protein.

In the methods described herein, an oral immunotherapy may optionally comprise an initial escalation phase. In some embodiments, the pharmaceutical composition of peanut protein for administration in an initial escalation phase of an oral immunotherapy comprises between about 0.5 and about 6 mg of peanut protein, such as individual doses of about 0.5 mg, about 1 mg, about 1.5 mg, about 3 mg, and about 6 mg peanut protein. In some embodiments, the pharmaceutical composition of peanut protein for administration in an initial escalation phase of an oral immunotherapy comprises between about 0.5 and about 6 mg of peanut protein, such as individual doses of about 0.5 mg, about 1 mg, about 1.5 mg, about 3 mg, about 6 mg, and about 12 mg peanut protein.

Kits for Oral Immunotherapy

The invention also provides kits, medicines, compositions, and unit dosage forms for use in any of the methods described herein.

Kits of the invention include an allergenic peanut formulation or peanut composition as described herein and, in some embodiments, further comprise instructions for use. The instructions for use can provide instructions according to any of the methods described herein, such as methods for continuing an oral immunotherapy for the treatment of a peanut allergy in a patient after missing a scheduled oral administration of one or more consecutive doses of a pharmaceutical composition comprising peanut protein; and/or instructions for orally administering to the patient a dose after the one or more consecutive missed doses of the pharmaceutical composition; and/or instructions for restarting the up-dosing phase. The kits comprise a plurality of pharmaceutical doses. In some embodiments, the plurality of pharmaceutical doses individually comprise the same amount of peanut protein. In some embodiments, the plurality of pharmaceutical doses comprises about 10 to about 45 doses of peanut protein, such as about 10, about 15, about 20, about 25, about 30, about 35, about 40, or about 45 doses of peanut protein. In some embodiments, the plurality of pharmaceutical doses comprise doses for administration during the up-dosing phase. In some embodiments, the plurality of pharmaceutical doses comprise doses for administration during the maintenance phase.

In some embodiments, the kit provides a label indicating that the allergenic peanut formulation or peanut composition is indicated for continuing an oral immunotherapy for the treatment of a peanut allergy in a patient after missing a scheduled oral administration of one or more consecutive doses of a pharmaceutical composition comprising peanut protein.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein.

Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase.

During the 240 mg peanut protein dose level, the patient reports to her medical provider that she had missed yesterday's scheduled dose. The patient is then advised by the medical provider to resume their up-dosing schedule by taking their next scheduled dose. The patient then self-administers the next scheduled dose of 240 mg peanut protein at home.

Example 2

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase.

During the 240 mg peanut protein dose level, the patient informs her medical provider that she had missed the last three consecutive doses. The patient is then advised by the medical provider to return to the clinic. The patient's medical provider evaluates the patient. Absent serious compounding or concurrent factors, according to the guidelines, the patient is then administered the 240 mg peanut protein dose in the clinic. The patient is observed for 60 minutes and sent home when no reaction occurs. The patient is instructed to continue self-administration of the 240 mg peanut protein dose for the remainder of that dose level.

Example 3

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase.

During the 240 mg peanut protein dose level, the patient informs her medical provider that she had missed the last five consecutive doses. The patient is then advised by the medical provider to return to the clinic. The patient's medical provider evaluates the patient. Absent serious compounding or concurrent factors, according to the guidelines, the patient is then administered a 120 mg peanut protein dose in the clinic. The patient is observed for 60 minutes. The patient is then given additional doses of the 120 mg peanut protein dose and instructed to continue the up-dosing phase at the 120 mg dose level by self-administration at home. The patient is instructed to return to the clinic after completing the 120 mg dose level to advance to the 160 mg peanut protein dose level again.

Example 4

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase.

During the 240 mg peanut protein dose level, the patient informs her medical provider that she had missed the last ten consecutive doses. The patient is then advised by her medical provider to return to the clinic. The patient's medical provider evaluates the patient. Absent serious compounding or concurrent factors, according to the guidelines, the patient is then administered a 40 mg peanut protein dose in the clinic. The patient is observed for 60 minutes. The patient is then given additional doses of the 40 mg peanut protein dose and instructed to continue the up-dosing phase at the 40 mg dose level by self-administration at home. The patient is instructed to return to the clinic after completing the 40 mg dose level to advance to the 80 mg peanut protein dose level again.

Example 5

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase.

During the 240 mg peanut protein dose level, the patient informs her medical provider that she had missed the last fifteen consecutive doses. The patient is then advised by the medical provider to return to the clinic. The patient's medical provider evaluates the patient. Absent serious compounding or concurrent factors, according to the guidelines, the patient is then administered a 3 mg peanut protein dose in the clinic. The patient is observed for 60 minutes. The patient is then given additional doses of the 3 mg peanut protein dose and instructed to continue the up-dosing phase at the 3 mg dose level by self-administration at home. The patient is instructed to return to the clinic after completing the 3 mg dose level to advance to the 6 mg peanut protein dose level again.

Example 6

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase. After the up-dosing phase, the patient begins the maintenance phase.

During the maintenance phase, the patient informs her medical provider that she had missed yesterday's scheduled dose. The patient is then advised by the medical provider to resume the maintenance phase schedule by taking their next scheduled dose. The patient then self-administers the next scheduled dose of 300 mg peanut protein at home.

Example 7

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase. After the up-dosing phase, the patient begins the maintenance phase.

During the maintenance phase, the patient informs her medical provider that she had missed the last three consecutive doses. The patient is then advised by her medical provider to return to the clinic. The patient's medical provider evaluates the patient. Absent serious compounding or concurrent factors, according to the guidelines, the patient is then administered the 300 mg peanut protein dose in the clinic. The patient is observed for 60 minutes and sent home when no reaction occurs. The patient is instructed to continue the maintenance phase by self-administering the 300 mg peanut protein dose according to the oral immunotherapy schedule.

Example 8

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase. After the up-dosing phase, the patient begins the maintenance phase.

During the maintenance phase, the patient informs her medical provider that she had missed the last five consecutive doses. The patient is then advised by the medical provider to return to the clinic. The patient's medical provider evaluates the patient. Absent serious compounding or concurrent factors, according to the guidelines, the patient is then administered a 120 mg peanut protein dose in the clinic. The patient is observed for 60 minutes and sent home when no reaction occurs. The patient is instructed to resume up-dosing by completing the 120 mg dose level by self-administration at home. The patient is instructed to return to the clinic after completing the 120 mg dose level to advance to the 160 mg peanut protein dose level again.

Example 9

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase. After the up-dosing phase, the patient begins the maintenance phase.

During the maintenance phase, the patient informs her medical provider that she had missed the last ten consecutive doses. The patient is then advised by the medical provider to return to the clinic. The patient's medical provider evaluates the patient. The guidelines prescribe a more stringent dose reduction for ten consecutive missed doses during the up-dosing phase. A less stringent dose reduction is allowed for ten consecutive missed doses during the maintenance phase. Absent serious compounding or concurrent factors, according to the guidelines, the patient is then administered a 120 mg peanut protein dose in the clinic. The patient is observed for 60 minutes and sent home when no reaction occurs. The patient is instructed to resume up-dosing by completing the 120 mg dose level by self-administration at home. The patient is instructed to return to the clinic after completing the 120 mg dose level to advance to the 160 mg peanut protein dose level again.

Example 10

Continuing an Oral Immunotherapy for the Treatment of a Peanut Allergy

A patient with a diagnosed peanut allergy is treated for the peanut allergy by administration of a pharmaceutical formulation of peanut protein according to an oral immunotherapy schedule. The up-dosing phase of the schedule has daily dose levels of 3 mg, 6 mg, 12 mg, 20 mg, 40 mg, 80 mg, 120 mg, 160 mg, 200 mg, 240 mg, and 300 mg peanut protein. Each dose level of the up-dosing phase is indicated for two weeks of administration, as tolerated. The maintenance phase of the schedule comprises a daily dose level of 300 mg peanut protein, as tolerated. At the clinic, and under medical supervision, the patient undergoes an initial dose escalation, progressing through doses of 0.5 mg, 1 mg, 1.5 mg, 3 mg, and 6 mg peanut protein with 20-30 minute intervals between doses.

The next day, the patient returns to the clinic where she is administered a dose of 3 mg peanut protein, which is the first dose of the up-dosing schedule. The patient is observed for 60 minutes after administration of the dose. The patient is sent home with additional doses of the 3 mg dose. The patient returns after 2 weeks and is administered the 6 mg dose under medical supervision. The 6 mg dose is tolerated and the patient is sent home with additional doses of the 6 mg peanut protein dose. This process repeats as the patient progresses through the up-dosing phase. After the up-dosing phase, the patient begins the maintenance phase.

During the maintenance phase, the patient informs her medical provider that she had missed the last fifteen consecutive doses. The patient is then advised by her medical provider to return to the clinic. The patient's medical provider evaluates the patient. Absent serious compounding or concurrent factors, according to the guidelines, the patient is then administered a 3 mg peanut protein dose in the clinic. The patient is observed for 60 minutes. The patient is then given additional doses of the 3 mg peanut protein dose and instructed to resume up-dosing by completing the 3 mg dose level by self-administration at home. The patient is instructed to return to the clinic after completing the 3 mg dose level to advance to the 6 mg peanut protein dose level again.

What is claimed is:

1. A method of continuing an oral immunotherapy for the treatment of a peanut allergy in a patient after missing a scheduled administration of one or more consecutive doses of a pharmaceutical composition comprising peanut protein, wherein the patient began an oral immunotherapy and missed one or more doses of the up-dosing phase or the maintenance phase of the oral immunotherapy, the oral immunotherapy comprising:
- (i) an up-dosing phase comprising orally administering to the patient a series of escalating doses of the pharmaceutical composition with a single dose administered on a daily basis, wherein the series of escalating doses administered during the up-dosing phase comprises doses of 3 mg to 300 mg peanut protein, and wherein a given dose is administered to the patient for at least a predetermined period of time before the dose is escalated, and
- (ii) a maintenance phase comprising orally administering to the patient a plurality of maintenance doses of the pharmaceutical composition after completion of the up-dosing phase, wherein the maintenance dose of the pharmaceutical composition comprise about 300mg peanut protein and are administered daily;

the method comprising:

orally administering to the patient a dose of the pharmaceutical composition after missing the scheduled one or more consecutive doses, wherein:
- (1) if one or two consecutive doses are missed, the dose administered to the patient is the same as the most recently administered dose;
- (2) if three or four consecutive doses are missed, the dose administered to the patient is reduced compared to the most recently administered dose, wherein the dose is reduced by:
  - (i) 25% or more, and the dose is administered to the patient under medical supervision, or without medical supervision; or
  - (ii) 50% or more and the dose is administered under medical supervision, or without medical supervision;
- (3) if five to seven consecutive doses are missed during the up-doing phase, the dose administered to the patient is reduced by 50% or more compared to the most recently administered dose;
- (4) if eight to fourteen consecutive doses are missed during the up-dosing phase, the dose administered to the patient is reduced by 75% or more compared to the most recently administered dose;
- (5) if five to fourteen consecutive doses are missed during the maintenance phase, the dose administered to the patient is 120 mg; and
- (6) if more than fourteen consecutive doses are missed, the dose administered to the patient is an initial dose of the up-dosing phase.

2. The method of claim 1, wherein the missed one or more consecutive doses were scheduled during the up-dosing phase.

3. The method of claim 1, wherein the missed one or more consecutive doses were scheduled during the maintenance phase.

4. The method of claim 1, wherein the pharmaceutical composition comprises defatted peanut flour.

5. The method of claim 1, wherein the series of escalating doses of the pharmaceutical composition administered during the up-dosing phase comprises 5 to 15 different dose levels.

6. The method of claim 1, wherein the series of escalating doses administered during the up-dosing phase comprises 11 different dose levels.

7. The method of claim 1, wherein the series of escalating doses administered during the up-dosing phase comprises doses of 3 mg peanut protein, 6 mg peanut protein, 12 mg peanut protein, 20 mg peanut protein, 40 mg peanut protein, 80 mg peanut protein, 120 mg peanut protein, 160 mg peanut protein, 200 mg peanut protein, 240 mg peanut protein, and 300 mg peanut protein.

8. The method of claim 1, wherein:
- (1) if one to two consecutive doses are missed during the up-dosing phase, the dose administered to the patient is the same as the most recently administered dose;
- (2) if three or four consecutive doses are missed during the up-dosing phase, the dose administered to the patient is reduced by: (i) 25% or more, or (ii) 50% or more, and the dose is administered to the patient under medical supervision;
- (3) if five to seven consecutive doses are missed during the up-dosing phase, the dose administered to the patient is reduced by 50% or more compared to the last administered dose and the dose is administered to the patient under medical supervision;
- (4) if eight to fourteen consecutive doses are missed during the up-dosing phase, the dose administered to the patient is reduced by 75% or more compared to the last administered dose and the dose is administered to the patient under medical supervision; and
- (5) if more than fourteen consecutive doses are missed during the up-dosing phase, the dose administered to the patient is an initial dose of the up-dosing phase.

9. The method of claim 1, wherein:
- (1) if one to two consecutive doses are missed during the maintenance phase, the dose administered to the patient is the same as the most recently administered dose;
- (2) if three or four consecutive doses are missed during the maintenance phase, the dose administered to the patient is reduced by: (i) 25% or more, or (ii) 50% or more, and the dose is administered to the patient under medical supervision;
- (3) if five to seven consecutive doses are missed during the maintenance phase, the maintenance phase dosing administered to the patient is 120 mg, and the dose is administered to the patient under medical supervision;
- (4) if eight to fourteen consecutive doses are missed during the maintenance phase, the maintenance phase administered to the patient is 120 mg, and the dose is administered to the patient under medical supervision; and
- (5) if more than fourteen consecutive doses are missed during the maintenance phase, the maintenance phase dosing is ended and an up-dosing is restarted at an initial dose of the up-dosing phase.

10. The method of claim 1, wherein the given dose is administered to the patient for at least two weeks of time before the dose is escalated.

11. The method of claim 1, wherein the patient is 1 year of age or older.

12. The method of claim 1, wherein the patient is 4 years of age or older.

13. The method of claim 1, wherein the patient is between 4 years of age and 12 years of age.

14. The method of claim 1, wherein the patient is between 12 years of age and 18 years of age.

15. The method of claim 1, wherein the patient is between 18 years of age and 26 years of age.

16. The method of claim 1, wherein is 26 years of age or older.

17. The method of claim 1, wherein the oral immunotherapy further comprises an initial escalation phase.

18. The method of claim 17, where the initial escalation phase comprises a series of escalating doses from 0.5 mg to 6 mg peanut protein.

19. The method of claim 18, wherein the series of escalating doses administered during the initial escalation phase comprises doses of 0.5 mg peanut protein, 1 mg peanut protein, 1.5 mg peanut protein, 3 mg peanut protein, and 6 mg peanut protein.

20. The method of claim 18, where the series of escalating doses are administered on the same day and spaced out by 10 minutes to 60 minutes.

* * * * *